(12) United States Patent
Giovannoni et al.

(10) Patent No.: US 7,947,867 B1
(45) Date of Patent: May 24, 2011

(54) **RIPENING INHIBITION IN THE TOMATO *GREEN-RIPE* MUTANT RESULTS FROM ECTOPIC EXPRESSION OF A NOVEL PROTEIN WHICH DISRUPTS ETHYLENE SIGNAL TRANSDUCTION**

(75) Inventors: James Giovannoni, Ithaca, NY (US); Cornelius S. Barry, Haslett, MI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 846 days.

(21) Appl. No.: 11/442,028

(22) Filed: May 26, 2006

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. ...... 800/278; 800/298; 800/287; 800/317.4; 800/290; 435/320.1; 435/410; 435/419; 536/23.6

(58) Field of Classification Search ........................ None
See application file for complete search history.

(56) References Cited

OTHER PUBLICATIONS

Bowie et al (Science 247:1306-1310, 1990).*
McConnell et al, Nature 411 (6838):709-713, 2001.*
Benfey et al (1990, Science 250:959-966).*
Benfey et al (1989, EMBO J, 8(8):2195-2202).*
Barry et al (PNAS May 16, 2006, 103(20):7923-7928).*

* cited by examiner

*Primary Examiner* — Stuart F. Baum
(74) *Attorney, Agent, or Firm* — John D. Fado; Evelyn M. Rabin

(57) ABSTRACT

To achieve full development of the ripe phenotype, climacteric fruits, such as tomato, apple and banana, require synthesis, perception and signal transduction of the plant hormone ethylene. The non-ripening phenotype of the dominant Green-ripe (Gr) and Never-ripe 2 (Nr-2) mutants of tomato is the result of reduced ethylene responsiveness in fruit tissues. In addition a subset of ethylene responses associated with floral senescence, abscission and root elongation are also impacted in mutant plants but to a lesser extent. Using positional cloning we have identified an identical 334 by deletion in a gene of unknown biochemical function residing at the Gr/Nr-2 locus. Consistent with a dominant gain of function mutation, this deletion causes ectopic expression of GR/NR-2, which in turn leads to ripening inhibition. A CaMV35:GR transgene recreates the Gr/Nr-2 mutant phenotype but does not lead to a global reduction in ethylene responsiveness suggesting tissue-specific modulation of ethylene responses in tomato. GR/NR-2 encodes a novel evolutionary conserved membrane localized protein of unknown biochemical function that has not previously been associated with ethylene signaling. Because GR/NR-2 has no sequence homology with the previously described Nr (Never-ripe) ethylene receptor of tomato we now refer to this gene only as GR. Identification of GR expands the current repertoire of ethylene signaling components in plants and provides a tool for further elucidation of ethylene response mechanisms and for controlling ethylene signal specificity in crop plants.

24 Claims, 7 Drawing Sheets
(2 of 7 Drawing Sheet(s) Filed in Color)

Fig. 5

SEQUENCE LISTING

<160> NUMBER OF SEQ ID NOS: 37

<210> SEQ ID NO 1
<211> LENGTH: 16234
<212> TYPE: DNA
<213> ORGANISM: Lycopersicon esculentum

<400> SEQUENCE: 1

```
ccctcgtaaa aactcgaaat tgatcaaact cggcgacgtt gatatatatg cccttattgt      60
tatgcaatct acgcccaacg gccaattaag tcctaaataa caatcataaa ctacaatacc     120
cacaaataat tcaaaacaaa agaatatatt aaacaaggag catgacccac ctgatcaaca     180
agcttttgat cttcaggagt ggcctcagca ccgcgatcaa gtgggctat ggcttcgaga      240 agctcctgct taaggctctc aatgtcttca cttttggtaa acaaaaacgg aaataaggaa     300 accctt gccc tcaatttcaa agattccggt acataattga cggccgtaaa atgatggaaa    360
aatgatctcc ttcttgaaca agaaagtagt agtttcggat ttgctgggaa agaagaatta    420 ataaagggg agattgggtg aagtttaacc ggagaagatg aagacataca aagagtagcc     480
attgttggtt aaaattttga aatagtatta gttcaattt ggtacacaca gttttgtcct     540
ggcgtggata aacatatttt cacacgtctt ccttagcttc ccgccacatt ttaataaata     600
tctcatatgc ttaattatta gagtcggttc cgttattcgg tatttacttt aaaaaaaata     660
tggtataata agtcaaacta attcaagttc agtttgattt tttaacgatt tattttaatt     720
caatattttt aataaaaatt tgattcttcg atgcattaaa gttttgaaac ttttactaaa     780
cattgaatcg aataatcaaa cttttgaaaa aataacaata atatcagact taaaaagtat    840
ttatgcctac ccctaaaaat aatacatttc actcttttt ttttattgtt ttaaacaaaa     900
aaaaaacatg tattttcaga aacatttata ttcccaattc ctaagaactt aatagaattg    960
tttaataaga agaaaaattt tttaaaaaaa ctccgttacc gggaatcgaa cccgggtctc   1020
ctgggtgaaa gccagatatc ctaaccgctg gacgatgacg gatgcttgtt gagaaaattg   1080
caatctttaa ataattaata gtcttatcct gaggcatctc tttatttttg gccatgtgaaa  1140 tcaagttaat gtaacttctt cttcttcttt ttaaatgttt ccttgaaggg gttatttaaa   1200
aaaaaatgga aaatgaggga ggggattacc acggagcaat ttgaactctc aaaggtaagg   1260
tgaaagttta ggtagtcaac caataaggta aatttaactt gaagttactt tatttgtttt    1320
atccgattgt ttaatgcttt attttatat tatcaaataa ggcttgtttt ggaaattttg    1380
agttaagttt gtaggaaata agtatgtttc ttatttttt agtatgtgag taaaaaatat   1440
tattctacaa cagttataca taatttagac atatattatg tgaggtggga gtgaaggcag    1500
aagtatgggt gtgttggata gtggtgagca tacaattgt ttttcaaggt ttagcttgtc    1560
caattggcgg tgatcttgtg atgtcttttt tctgtgcaag atacaacgat gaatttcttt   1620
tagttatcgt tctaaataaa tgagattaac ccttaaatta atcgattgat tcaaagtacg   1680
```

```
aaaggattga ttgaagtttg aaatcaatta aggactaatg ccaagcaagt agctgttgca    1740
agattgaacg tctagtatct atttcacgac actcccaaac tcttataaag gtcggtggaa    1800
gaaagttctt ctcatatttc ttaccgctcg ttatcataac aattgttcac tctttcgact    1860
tcttctattt taaaaagtca cttgtaaaac tagttaattt ttacttctat taggaaagtt    1920
aattttctca tttttgatga agttgttatg catagaaatc aaatttgtca gtcttcctca    1980
aatttatttt gaaatataaa taaaaatggg aaaattatat ataatatgac aaaattaata    2040
aatcaaatta aatgttataa ccatgcttta atttaattgt gccttgtcgc aaactatttg    2100
tcagtcacct ctctccttca aactctcgct cgctcactct cacttttata caaacacaat    2160
tgtataaatt gcattctgtt tgtatgaagc gagaaaaaaa ttgtatatat acatatattt    2220
ttttctcctc tctctcctct ctcagatctc gctcgccact ctcgtagatc tcgctcacca    2280
ccctcgtcca tatcgtttat acaaacataa atgaaatgta taaattgcgt ttttgtttgt    2340
ataaagcaac agaaaatttt atgtgtatac acttggaaat acacatattt ttgtcatata    2400
cacttataat tatacaatat aaaaaaaaat tcctgcccaa ttttcttttg ttttttctctc    2460 tttcttttttt tatacataca caaattatac aattgatttg tatacaactt ctttcttttg    2520
tatatgtata gcgaattata taattgattt ctttgtatat gtatagcgaa ttatacataa    2580
ttatatttgc tatgaatgac aattatgcaa actttgctat tacgtacaaa tataaaattt    2640
gtatttacta tatgtgaaag ttgctaaaaa aataattata ttttcatgca ttttgtgcaa    2700
acttaaccga tgaatatttg tcaattttcc ttaaatgaaa gtcgttttaa aaaataaaaa    2760
tctgaacctt ttttttttcaa aaaataaatg atgaaagtcc ataagttttt ataaagattt    2820
tttttaaaaa aaaattattg tcttttttgac attatccttg gttttatcgc caattttcac    2880
ttgtttttaa caacgctaat gagatttttt ttaaaaaata tataatgaga ttttaaaaaa    2940
aaatatatat ttataattaa tcttttattg cacaaattct tatcaaatct aatagaaata    3000
gtttgctaaa taatttgatg gactaaaaat gttaaacttt cagcgatctt aaaggatttc    3060
aaccttgaaa tacattctta acagaatatt tttaatctac cttcaaacat aaaatatcat    3120
ttttagaaaa aattatgaga aagtcaaagg atcaaaacta taaaatgtat acttggaaga    3180
gactaattgt atgcaacttt tccatgtgtt gttcctttct aatatcattt tagaaactaa    3240
tattgtttta tgttgtatat tttaggattt aatgaaacaa ttttttgata tttataatca    3300 atctttttttc acaattcttg tcaaatcaaa ttagaaacat tttgtttgaa aattgaaaat    3360 tttaacttttt gacaatctta aaagattgaa acctaaggga gtattattta gtctacccctc    3420 aaacataaaa agaccatttt tgttgaatta agacaaattt aaaggattaa aattataaca    3480
tctatactta agggactatt ttgagtgttc cctcaaacat aagggaccat ttttataatt    3540
ttctcatatt ttttttttttt ggccctattc caatttaaat gcaatgaaac cccaagactc    3600
agatgagaaa ccgataaaga agaacgggaa gaagaaacat agaagagctt gaggaatcat    3660
gaatgctcca ccgcatgacg tatgtaaatg tcaatggcgt attcacccctt ctctctattc    3720 ggttgtcttc ttctttggta agcaaaagaa gaagaagacg taatagagaa actgaaagaa    3780
aaaagggaca aaaatcaagc tgtcccggca tttactcttt gttttctacc agctttctct    3840
acttttgtct gatcttccga aatgtaaccg cttcactcat atctaagttg ctgattgtag    3900
tatcagtttc ttgacctcgt tgtactctgt gagttcccctt tcttgattac tcaatgtact    3960 taaattttttt catttaatca ttgttttttgt tgaatttgtt aaaatgggtg ttggtttttc    4020
tgtacgtaga tgactggaat tttgaagatt gcggatttga ttgctgagaa gacacattaa    4080
```

```
ggttgctact agttttttt  gctacttatg ttactgctaa tttacttgca atttgtttt   4140
gatttctgg  aaatttagtt ctgcaaagcc ataaggatgt gtgggtatac tataagtatg  4200
attaagaacg aagttctagg ggactattgt gttgagatgg tttggatatg tgaagaggag  4260
gtgttagggc gtgccagtga agaggtgact agactttata ggatgtggga gtgaactttt  4320
tcttgaattg ggtcaaagtg atcaagtttg tcgaggccaa tcattgctaa gaattaatgg  4380
aaaacttggg aaatagcttc tgctaattgt aaattagcct ttaatacaat gtccacatgc  4440
tgtgtaatta aatatattat atgtttgaga agatatgatg gccttttctt cctggcagtc  4500
tctcgttaga atcggaattt ctagtttagt gatgatgatg tgtttgattg cccctccttt  4560
cccttgttag ttattttctt gttcgtatgt gacattggcc tgaagggatt tatgcagcta  4620
ttctattaac tacatgagct agggagatct ttttccagca agtccttgcc caaaagtgct  4680
tttatcgttt ctttgtgtcc tatactgaga agggattttg cataatatgt gattgatatt  4740
taatttgcga ccagatgttg aagtaatgtg aactgtagag agaaaagag  atcaaattac  4800
ttactaatgc agtaaaagga tcttattagt cattctgttt taaagaacca ttcccattga  4860
aatttgctat ggatcataat gtaattgtgg acataaattg cattttatgg ggttcatctt  4920
catctttcat gttgccttca ggaatgctaa agcagactgg tctttacaac ttcacctatt  4980
aatttttcc  tacttggcaa ctgaaagaag taattaagta gaattgcttg aagatagggg  5040
tagatgatct tggctaggat gccttatac  tcgttatgac ttccttgtag aggtgaagaa  5100
ttggtgagag agattataca cttgtactta attaaactat tatatatatc tttctgataa  5160
aaaaaagtat atcagacatt ctaagttttc aaatttacta tgctgtatga ttactaagtg  5220
gtgtataaac ccaaccaaaa tagtctgttt ggcctggtcc aaatcttagt ccattgtgac  5280
tagaattctt agtcaagcct ccactgtggg gcatatataa atggacaaaa attgatccgt  5340
atatcagttc agttcacaca tctctctact ttctggttgt cttgttactg gtaaattaaa  5400
agacagaagt gaacataaaa gagaaacaga aaaaagggac aagtgtcaag tggacaacaa  5460
aatgtgacct gtacttactc ttgttttcta gtgttcctca gttgggattt ccccttactc  5520
ataagtcata actgtaacga ttcgttgata tctaagttga tgattgtgtc tcttcactgt  5580
gttttttgct tgttattctc tgtaattatt tccagggttt ctttcatcct tccctatt    5640
tctaaaattg attcacatta cccaatgcac ttgcattgaa tcaatttgat ctttgtttt   5700
gttttgttaa ccgggtgttg gttttctgt  acttaggtaa ctttggaatt ctcaagattg  5760
tattttggtt tgccaagaag acacgataag gttgatgatt gttctttact ttctttttgtc 5820
ccttatgtta ttgcaaatgt atctacattt ttaccctgga atttaggtcc tgaaatccat  5880
ctcgaagact ctttgtcctt ggctacctta ggtaggagtg tgctcatttt ctagaatttg  5940
gttagcatcc aagtttgaaa tgtcaaatca ttgctcaaaa ttaatgaaag actttgaaca  6000
atagcttgaa ctaattgtag attagcctat aaaacaatat caatcagtta tactcctta   6060
gtatcttaga tctttcagaa gaagtgttcc aactttctct ctctgtcagt ctgtcattag  6120
aatctaattt tgtggaagtg ctggtgataa tgcctttatt agcccccttt cccctcttgc  6180
tagttctttt aattgttctt cattgacatt tgcatgaatg gattccttca gctctgctgt  6240
taactacatg agctagggag aggtaccagc tcaaagggt  ttttctcttt ctttgtgatt  6300
tttacttaaa agggcttttg aatgacttga tatatgattt gccaacagat gttaaagtta  6360
tgtgaacttt atgattcagt aagaaagaaa aatcatttct aaagaaaaaa aagtaattta  6420
gtaaagaaca tatgttaata attgaatctt tacagaacca ttttgtataa ctcggactct  6480
```

```
ggtcataatt aatgtaatgg gtttcatttt catatttctt cttcttgcct tcagaattac    6540
caaagcagat ggatctttgc ctataagttt tttccttttc agatctgaca aaagtaagta    6600
caagaattta agatatatga ttttttttct ggggtgcatt tcatactagt tatggctttc    6660
ctttattaga gatgtagttt aggttactac ttaatgaagt aattatatct atatctatga    6720
gaaatgtaag tatttcacta atgacacaca aatacattag atgtttgaat tgggggtatg    6780
gctcaaccat tttcttctat caagtctact tgaccttttt ttagatcagg tgaaggattt    6840
gattaataat aaaaagtaaa ttcaactatc tattaaagag ggaattctta cactcatagt    6900
gtacctgaag ataaacaagt tataacttct tcaaatcatt cttacgatct taaacaattt    6960
tctatttctt ttaatccaat taatctaaaa ggacactctt atcaaccaaa aggaaaaaaa    7020
ggaaggctca atgctgagat cttgcttttg aagcttttaa gatgatcctt ataatagtat    7080
gggtaaacat ggatatccat attatccatt gggtaattcg ttttaccca tttaaaatat    7140 gagtcgagtc gaatcgagta ttttccccat ttttatataa ctcattcttg atcgacttat    7200
attcgattcg agacgggtaa aggtgtggat catccccttc tttattgtag tctagcttcg    7260
agttatggtg caaagtattc aattggtttg gtatctcata ggtgattcca agagttgtat    7320
aagagctaat gatcgactat aattatggga gaaggtgcat ggcatggact attgctccac    7380
tagctatctt gtgggatatt tggagagaaa aaaataaaag agcttttgaa ggagtagaga    7440
tgagttttat tccgttgata agtagccttc tatttcttct tttcttttgg tgccccatg     7500 aagtcgtata ttgtatataa gattgggtgt ctttgatata ggaccatatc ttttgtaggc    7560
ttactaccct tttggtatac ttctcgtata tggatactct ttgctttggt ccatttattg    7620
attaatattt tacttgataa aaacaaaaac aaaaatctta ttgctgaaat tcaaaaagat    7680
gttctcattt catgtttacc tatatttctt acaagatctt taactaaaat ttgtagacat    7740 tttttttgtac aacacgaacc aaccatatga atccggttgt ggatatagag ctatgtttgt    7800
cttgctctca tcatcaaaaa caaggttcca tgattgtgtt tgagactgca atgcaattag    7860
gggttgacct taatcacaat aaattgaatt accgaagttt gatttactgt atcagaccgg    7920
cttttcaaag ttcggtattt ggtatttact tctacttgca ttaatttacc gaaatcagac    7980
tttggaaata ttaaattgaa taaccaactc tatccccaa agaacttgtc tattttgtt      8040 tgtggcaaca attttcatgt cctcgtcgta aatattcact aagcatatta gcttattgat    8100
ctaaccaaat tcaccaagaa cgcaagtttg agaaagttgg ctattgatct aaacatatct    8160
tgtaaaatca tattttcctt caatacgtaa ttaccaaatt acctgtacta aagttcgata    8220
tattgtaata attgatttct tttttcaatt actaattatc cagttaacgt ttactgaaac    8280
caaactttgg agaagggaat cgaataccga acggccaccc ttaaatgcaa taaggtgtgc    8340
ttagtatctt ctccacactt ttctcatgat cataccaact cataacaatt ttcagatttc    8400
cttattttag ctgccattac catttcaccc caatattatc aacaacgaaa gaaagctact    8460
ttcgttagcc atcttggtac tctgcattct tccgcaccaa gtgctattat tttaagcgaa    8520
tgactttcca taggctccct tactagtgaa tccaagattt tcactaacag ggttcagaaa    8580
ataaaatgta gtgcatggag attgaactta gaacctcaag gtgaattttg aaccccctaa    8640
accactgagt caacctctag tttgtgttta gggaattcaa aatctatata tatgcataaa    8700
aaattacctt atgtatacaa tgtaattttt tgtcgaggaa gtttaggtga acaccatgac    8760 tacccccctat attctccctg agcaccgttc atatccacct ttctattttg ttctcctatt    8820
gaggtgtcat aaacttttttt tttgaaactc ctagatctta tcttattcct aatcctatat    8880
```

| | |
|---|---|
| gttcgtgaga ttccctgtct tatttatttt cctaaataat caaccatcgt tgtttctcta | 8940 |
| ttagtctcta ttaaaacaaa tttaccattt tgcggaagag tatcttgtac tatcctatta | 9000 |
| aaacaaattt acctaaaatg ctagttttt tggtaaaac caaacatagt gaagtagaac | 9060 |
| ctattttgaa aataatctta atatgtgtgc cacgacatag aacatggtgg agcagaaccc | 9120 |
| aaaatagtgc atctttaaag gattagacgg gtgtggcaac attttggag agtacgtttt | 9180 |
| caaaaccaa aagaaaaag gaaaagact ctaaaacaga ctaaaagga aagtaaggcg | 9240 |
| aataaactga aatgaaggga gtatcagaga gaatgaatct cgaagagcct catgtcaaca | 9300 |
| tattacttaa tacgttctta taatcatata ctccatccat ccactttat ttgtcatgtt | 9360 |
| gcccttcgaa agtcaatttg actaatttca agttaaatta gatcatttta atttaacaaa | 9420 |
| aactttagat tttcaaaagc tatacgaaac gtactataaa ttacaatttt cttatatcat | 9480 |
| atgatgaaaa aatacattgt aaaatgttag tcaaagttct tatagtttga cttaaaaaaa | 9540 |
| gaaaactatg acaattcaaa gtggacggag gtagtatatt ttaggattta ctattctata | 9600 |
| ttcaaattat tatttttga atatttgcga gaaactggat gcgaaggaac tcttgtccaa | 9660 |
| ttttatagta gaaatggact taaaaaacaa cgtaaactat aacccaaaga accatactcc | 9720 |
| gtcctaatag cctatgtagt atgatctcat tgaataattt tctcttgaca ccctccattt | 9780 |
| cataccattc cttcccttct tattgagatg tcatatattt tctatttgaa ctcctcaaac | 9840 |
| tttgactttt tcgaatcttg tacggtctgt ctctccatga aacttatctt gacgtaattc | 9900 |
| ccctatctgt gatcatcaat ggagctctta aagttttttt tccctatatg caaaggatta | 9960 |
| agacctcaat ttcaaaaaaa aaaacaaagg attaaaacat ctagctctta agaaatacca | 10020 |
| ttagttgagg cattattcgt taatgctaat ttgtccatat tagatttcag gcacaagtag | 10080 |
| tttcaccact ctaagtttgt actaggaagt taaacagggc aacgataggc taagttgcta | 10140 |
| ggacttgagt gtgggtgtcc tacatgtgtt acaaggtgag tatctagaga ttggatcctt | 10200 |
| catgattggg atttggcgaa aaagtgattc aaatatctaa caatagagtt atatgtctaa | 10260 |
| actatgactc tgagacatta tgtggaaaat ggagaactta caaagtattc tgagaagaaa | 10320 |
| attgataatc ctaggagaga aggaaatgaa ctagcgcaga aagttctata tacaagctat | 10380 |
| tatatttatt ctatttcacc ttagcttttg ttttgattat ggagattatt gtatttatct | 10440 |
| cgaatttctt tgtcgatttt ggtcaaagta ctcaaaattg gttgaccaaa ttcggcgcgg | 10500 |
| atcctacact cacacccaca cccacaccca catccacatc catgccatgt cgacaggggt | 10560 |
| gtggcaccga aagagaagag tccgagtaac ttagttgata cgtgacaacc taatgaacgt | 10620 |
| gtcaaagtgc tttaattgca ccttatttta tagattttat tcacatttat gcttcttttt | 10680 |
| tccactgtgt aagtcgtgcc taaatgatac cttttcataa aaaagaaagg gaagtagtaa | 10740 |
| ccattaagtc cagtacaatt gtcacccaaa taagacaagg aacgttattc aatgctactg | 10800 |
| cacttttctc tctacaactc tctactgctt ccccttagga ttttggaaac tgactttata | 10860 |
| ccattataga gatattgcat cataacactt tccaatctat gactcaatca aagggttat | 10920 |
| atttttccat tatctctttt cactgtagat agtattactg gaatcaagcc aagtgagtga | 10980 |
| aatgtttatt ctgcttgttt tgcgtcattt ttgaataagc atactgtatg agttaccact | 11040 |
| acctagcctg aagtttaaag gcttaggcct cttctttttt cccttatttt ccccataaag | 11100 |
| gtgactactg ctataaatat catctacaca aaggcagttg taggtgtcat acacaattca | 11160 |
| aaaagcaaac acagtgtatc cttgattctt cttacaagga ttctaaaact cttctaaaat | 11220 |
| agagtttgag tcatttataa atttctcttt ccaccaaaag taaaccagaa gcatacaatt | 11280 |

```
cattttatct tctgagtaga actataccta ttctaaaagc atcttgattc tttttcttcc    11340
tcttttgggt attggttcaa aacctgatgt gcaacctaat tttatatagt actttcttta    11400
ctagagaggt tactttcact tgacatacta attattgttt ttttccttat aaattactac    11460
tattatttaa ttgaaaataa aaactctaag ctcaaaaacc tttctgttca ttgataggtt    11520
ctcagctcca cttcctatca gtagagtaag aatttgtgca tcaacttcta gtgcataaat    11580
taatgttttt cattgtgacg tgacataaaa tgggtaaagg aacttgcaac agtgccggag    11640
ttttaattgc tataattcca agtcttatcc gatgcatcat tgatgcatga gtgtaattgg    11700
cctatgaaat cttgcctttt tagctgattt ggtgataata tcgactacaa actgggaaca    11760
tcaagctaca gcctgacgtt actttcatag tgttacaaaa tgctggtggg attttttct     11820 tgatttgcag tgttttgct cggtagcaga tgagtatgaa ttacagaggc atgattaagg     11880
gttggaactg ataggatatg ggtggatgaa agttgtttgc tgcagcaatg tttattcgga    11940
aataagaaag gagaaataag ggtcctatca tccgatagag tgaaagggaa aacttatagg    12000
tagcagtgca tattttatat tctgcatcta taaggggcca aaagaataat tcatgaatat    12060
atgttaaact aaagggtcaa attgacataa aatgatgttc tagttcatat gctgtaattt    12120
gtaatgcatc caatggaaca tgtttatgaa tattgagtct actagtcttg aaagtcagtt    12180
gagtagagct ggactaagct gagctcaagt agcttatagt ttgtcttggc tcggttacaa    12240
ttatggtaag atttcagag gtacattaat cctatagcaa tcgttcttga catcagtcta     12300
agaattctta gatgtggcta cctcttcggt gttccaatga ctattcttta tgtgtctcct    12360
gatatcttat tgtgaagcat tgtggtcaaa tgaattcttc ttatatttga aatctaggga    12420
tatttgtata ttgaacttaa aaagtgtgga aatacagaat aaagtatata tatatatata    12480
tatagagaga gagagagaga gagagaagct ctctgaataa tgtgattttt aattgctgtt    12540
ctgccaaatt tatctcaaag aatgattgat cagatatgat atcagagatg acttgtcaaa    12600
tatctttcat gtatttgcat ataaatatat ccagttagaa gatttagtttt catacaggtt    12660 gagctcttat tctggctatt ttggactgta agaagtggct tttctcctaa gtaggagctg    12720
ctaagtagca aatgttgata ttgtttattc ttttgtgttg agtaattctt aattttactt    12780
tggtacactt cagcatttag attaggaccg tattctgaat catcattcct tagttggaac    12840
ggctgagact ccactgttta tagtgactgc tggccaggct taccttgagt ttaagaatat    12900
agctttagtt tttgatgact agagggtgta acgagatgat atccctttc ctatttaaca     12960 gggaatctca ttcttctagg aacgacgaaa ctgtaccttg ctatatgctg ccaagaagat    13020
atcctcagat ggatgctaat cctagtaatg ggggtgaaag ggataatgct ttgcgaggaa    13080
ttctgcagga cttatggcca ctggatgaaa ttgatccaag cactcaaaag ttcccttgtt    13140
gccttgtttg gactcctctc cctgtgattt cttggcttgc accttttgtt ggacatgttg    13200
gcatatgcag ggaggatggt accattgtgg attttttctgg agatagcatg attcattttg   13260
gtcagctctt ctatggaact gtagccaaat actatcaggt agacagacag caggtatgtg    13320
cccatgactg ctttttatcca ttccaaaatc ccacccgatc cccataaaga gaaagtagtg   13380
agaaaagttc aatggtgtgc ttacagtaga atctcttcaa tgactcataa aaaatgacaa    13440
gtgatttttg gtaactctct ttatcaactt tgctatgctt aaacagtgct gttttgctcg    13500
caactttggt ggacacacat gccgtaaggg ttatgaacat gttgtatttg ggacagcagt    13560
aagtggggat gatgctgttc agttgtttag gcgcaccttt gagaacagaa acttcaaagt    13620
tttcagttgc aacggccact cattcgctgc tgattgcctg aacctgctat catttagagg    13680
```

```
atcaatgcgc tggaacatga ttaatgttgg agctcttata atgtttgagg gaaagtgggt   13740
cagtcgctgg tcaatgttac gatcatttct gcctttcatt gggatacttt gcttcggcta   13800
tttaatgatt ggatggatgt ttccaattgg tctgctctcc tttgttattg ggacttttgg   13860
atggtatgtc atgatctgtt actgttgcaa gattgaggat gacaattaga accttgtgct   13920
gttggttcta gtcttttttag gtgtttgaga aagacactca aaagtgctct ttcctgaata   13980
aagtctcttc ttgtgagaga actctactta ttttctgttg tattgtcctg tgaaaacata   14040
ttatattagt taatgtcctg tgttgtaatg taatgtcaaa acatattatt ttagttaatg   14100
tcctgtgttg taatgtaatg tgaaaacata ttatattagt taatgaccag tgttgtaatg   14160
caatgttaaa acatagagta ctatatttag ttaatgtcca gtgttcctgt ccatttatgc   14220 agttttttaca acaaagaata ttgttttagt tttgacaagt tctcttggaa aattgtgtgg   14280
taaaagaaag tactggttag tctttaagta atccacaagc gcctctcgac tagggatgac   14340 aatgggtgg cgtgagttaa aggttgttct gggctggtga aagcaggtga tgtgtaatta   14400
aggttgtgcg gacgggtgga agcagatttt cttatactaa tgcggagctg tttaaggta   14460 tagcacgtga tttcaaattt attataagag ttatagaaca ttaattatta agataatttc   14520
tttaaaatta ctaaaatatt taagatatta aatgaaaata gtttaacaaa aaaaataata   14580
caatttctta cgtgtttcac atttgacttc taaaattaat attttaattc aatattttat   14640
cgtatttatt tttatgaatt ttatttttagt attaaattaa actataaaaa agaaaatatt   14700
taaaaaatta cggaattgat ctatgtggga aggatggggt aaattgaaaa tgaaaaaaag   14760
ttgttaaagg caaaaaaatt actccctcgt gagttaagtt caactcgccc aacaccgccc   14820
cgttgccatc tctaaaactca aagtcctcaa ccatagttaa ttttttccaag cagaatgcaa   14880 cattctcttt cattgaatta aaaaaatgag attttttttc ttttaaatta atatatcact   14940
ttcaaaatta atatctttta tataaatata ttaaatataa attgagtaaa ccagtttttt   15000 ttttttttgga tatttatgct gatttttctt agaggaaaat atattgattt acagaagtga   15060
taaaattaat tgaagtgtac aaatcggact taaaaaggac aaaattctta gtattaatta   15120
ttatattacc ttttacgtag gcagacatcc cataaaaatt aaaattagta ctagcatata   15180
tttaacactc aattaaataa aattatttcc aaaaatcagc aaaataatat ttttataatg   15240
ttaatattat aaatgaaaat gaaaaaaaaaa aatgaagtaa aactgtttcc tatgaggaag   15300
gaatccgttt tctctttctg cttcttcccc aagtatttga cagatagtga aacatctctg   15360
tgtgtctata taccccccacc cccaccccac cccaccccccc accccaggcc actcggcgga   15420
gaattagtct gttgagaact tttgaatcgg actgtttctt gagaattgga aattcttgta   15480
tttctgtaag attactttt cttcactttt tgattgaatt ctagagatgg gtcttgacgt   15540
ttcggcactt tgatttactt tcttgaaata aatgatcata tcttgaattg gggttttttt   15600
tcaaagacca ctgttcatgt tgtgtttttg tatgttcttc tgttgtctgt taggagaatt   15660
ctaaggtctg tatggaattt gcaatttaac actagagcag ttctgatttt cttgaaaatt   15720
tctgtttttc ttgaaaattc cgattttctt gaaaagttct gattttattt tcttgaaaaa   15780
gttttgattt tctggaagga aatagattaa aaaggggaa aggagatcct gattttctgg   15840
gaatgcttgg gtttggtgct atttagtcag aaattgtact ggcactcttg aatctctcag   15900
ttttttgttg attataacga ttttttttttt taaaaataac taaggtggtg gctgggccta   15960
ccgtctgggt actggtatct tcttggtgat aacaaaggtg aaaggtgctg gtagtactag   16020
atagctctgc cagatattg cgtccttcca ctagtgttgg aacaaattct gcccaccatg   16080
```

| aattaggtag ataggaaaat tgtacatggc tttttattta ttgtggaaat cttacctcta | 16140 |
| atggtttcat tccaacttca tttgtacctt gagtactaca tttttttatt ttgatgactt | 16200 |
| gaatcttgat tctagagaaa agctattttt tttt | 16234 |

<210> SEQ ID NO 2
<211> LENGTH: 1451
<212> TYPE: DNA
<213> ORGANISM: Lycopersicon esculentum

<400> SEQUENCE: 2

| gagaaaccga taaagaagaa cgggaagaag aaacatagaa gagcttgagg aatcatgaat | 60 |
| gctccaccgc atgacgtatg taaatgtcaa tggcgtattc acccttctct ctattcggtt | 120 |
| gtcttcttct ttggtaagca aaagaagaag aagacgtaat agagaaactg aaagaaaaaa | 180 |
| gggacaaaaa tcaagctgtc ccggcattta ctctttgttt tctaccagct ttctctactt | 240 |
| ttgtctgatc ttccgaaatg taaccgcttc actcatatct aagttgctga ttgtagtatc | 300 |
| agtttcttga cctcgttgta ctctatgact ggaattttga agattgcgga tttgattgct | 360 |
| gagaagacac attaagggaa tctcattctt ctaggaacga cgaaactgta ccttgctata | 420 |
| tgctgccaag aagatatcct cagatggatg ctaatcctag taatgggggt gaaagggata | 480 |
| atgctttgcg aggaattctg caggacttat ggccactgga tgaaattgat ccaagcactc | 540 |
| aaaagttccc ttgttgcctt gtttggactc ctctccctgt gatttcttgg cttgcacctt | 600 |
| ttgttggaca tgttgcata tgcagggagg atggtaccat tgtggatttt tctgagagata | 660 |
| gcatgattca ttttggtcag ctcttctatg gaactgtagc caaatactat caggtagaca | 720 |
| gacagcagtg ctgttttgct cgcaactttg gtggacacac atgccgtaag ggttatgaac | 780 |
| atgttgtatt tgggacagca gtaagttggg atgatgctgt tcagttgttt aggcgcacct | 840 |
| ttgagaacag aaacttcaaa gttttcagtt gcaacggcca ctcattcgct gctgattgcc | 900 |
| tgaacctgct atcatttaga ggatcaatgc gctggaacat gattaatgtt ggagctctta | 960 |
| taatgtttga gggaaagtgg gtcagtcgct ggtcaatgtt acgatcatt ctgccttca | 1020 |
| ttgggatact ttgcttcggc tatttaatga ttggatggat gtttccaatt ggtctgctct | 1080 |
| cctttgttat tgggactttt ggatggtatg tcatgatctg ttactgttgc aagattgagg | 1140 |
| atgacaatta gaaccttgtg ctgttggttc tagtcttttt aggtgtttga gaaagacact | 1200 |
| caaaagtgct ctttcctgaa taaagtctct tcttgtgaga gaactctact tattttctgt | 1260 |
| tgtattgtcc tgtgaaaaca tattatatta gttaatgtcc tgtgttgtaa tgtaatgtca | 1320 |
| aaacatatta ttttagttaa tgtcctgtgt tgtaatgtaa tgtgaaaaca tattatatta | 1380 |
| gttaatgacc agtgttgtaa tgcaatgtta aaacatagag tactatattt agttaatgtc | 1440 |
| cagtgttcct g | 1451 |

<210> SEQ ID NO 3
<211> LENGTH: 1235
<212> TYPE: DNA
<213> ORGANISM: Lycopersicon esculentum

<400> SEQUENCE: 3

| aatcattgtt tttgttgaat tgttaaaat gggtgttggt ttttctgtac gtagatgact | 60 |
| ggaattttga agattgcgga tttgattgct gagaagacac attaaggtaa ctttggaatt | 120 |
| ctcaagattg tattttggtt tgccaagaag acacgataag ggaatctcat tcttctagga | 180 |
| acgacgaaac tgtaccttgc tatatgctgc caagaagata tcctcagatg gatgctaatc | 240 |

```
ctagtaatgg gggtgaaagg gataatgctt tgcgaggaat tctgcaggac ttatggccac    300
tggatgaaat tgatccaagc actcaaaagt tcccttgttg ccttgtttgg actcctctcc    360
ctgtgatttc ttggcttgca ccttttgttg gacatgttgg catatgcagg aggatggta     420 ccattgtgga ttttctgga gatagcatga ttcattttgg tcagctcttc tatggaactg     480
tagccaaata ctatcaggta gacagacagc agtgctgttt tgctcgcaac tttggtggac    540
acacatgccg taagggttat gaacatgttg tatttgggac agcagtaagt tgggatgatg    600
ctgttcagtt gtttaggcgc acctttgaga acagaaactt caaagttttc agttgcaacg    660
gccactcatt cgctgctgat tgcctgaacc tgctatcatt tagaggatca atgcgctgga    720
acatgattaa tgttggagct cttataatgt ttgagggaaa gtgggtcagt cgctggtcaa    780
tgttacgatc atttctgcct ttcattggga tactttgctt cggctattta atgattggat    840 ggatgttcc aattggtctg ctctcctttg ttattgggac ttttggatgg tatgtcatga    900
tctgttactg ttgcaagatt gaggatgaca attagaacct tgtgctgttg gttctagtct    960
ttttaggtgt ttgagaaaga cactcaaaag tgctcttcc tgaataaagt ctcttcttgt   1020
gagagaactc tacttatttt ctgttgtatt gtcctgtgaa aacatattat attagttaat   1080
gtcctgtgtt gtaatgtaat gtcaaaacat attatttag ttaatgtcct gtgttgtaat    1140
gtaatgtgaa aacatattat attagttaat gaccagtgtt gtaatgcaat gttaaaacat   1200
agagtactat atttagttaa tgtccagtgt tcctg                              1235

<210> SEQ ID NO 4
<211> LENGTH: 243
<212> TYPE: PRT
<213> ORGANISM: Lycopersicon esculentum

<400> SEQUENCE: 4

Met Leu Pro Arg Arg Tyr Pro Gln Met Asp Ala Asn Pro Ser Asn Gly
1               5                   10                  15

Gly Glu Arg Asp Asn Ala Leu Arg Gly Ile Leu Gln Asp Leu Trp Pro
            20                  25                  30

Leu Asp Glu Ile Asp Pro Ser Thr Gln Lys Phe Pro Cys Cys Leu Val
        35                  40                  45

Trp Thr Pro Leu Pro Val Ile Ser Trp Leu Ala Pro Phe Val Gly His
    50                  55                  60

Val Gly Ile Cys Arg Glu Asp Gly Thr Ile Val Asp Phe Ser Gly Asp
65                  70                  75                  80

Ser Met Ile His Phe Gly Gln Leu Phe Tyr Gly Thr Val Ala Lys Tyr
                85                  90                  95

Tyr Gln Val Asp Arg Gln Gln Cys Cys Phe Ala Arg Asn Phe Gly Gly
            100                 105                 110

His Thr Cys Arg Lys Gly Tyr Glu His Val Val Phe Gly Thr Ala Val
        115                 120                 125

Ser Trp Asp Asp Ala Val Gln Leu Phe Arg Arg Thr Phe Glu Asn Arg
    130                 135                 140

Asn Phe Lys Val Phe Ser Cys Asn Gly His Ser Phe Ala Ala Asp Cys
145                 150                 155                 160

Leu Asn Leu Leu Ser Phe Arg Gly Ser Met Arg Trp Asn Met Ile Asn
                165                 170                 175

Val Gly Ala Leu Ile Met Phe Glu Gly Lys Trp Val Ser Arg Trp Ser
            180                 185                 190

Met Leu Arg Ser Phe Leu Pro Phe Ile Gly Ile Leu Cys Phe Gly Tyr
```

```
              195                 200                 205
Leu Met Ile Gly Trp Met Phe Pro Ile Gly Leu Leu Ser Phe Val Ile
        210                 215                 220

Gly Thr Phe Gly Trp Tyr Val Met Ile Cys Tyr Cys Cys Lys Ile Glu
225                 230                 235                 240

Asp Asp Asn

<210> SEQ ID NO 5
<211> LENGTH: 334
<212> TYPE: DNA
<213> ORGANISM: Lycopersicon esculentum

<400> SEQUENCE: 5 ttttttttt ttggccctat tccaatttaa atgcaatgaa accccaagac tcagatgaga      60
aaccgataaa gaagaacggg aagaagaaac atagaagagc ttgaggaatc atgaatgctc    120
caccgcatga cgtatgtaaa tgtcaatggc gtattcaccc ttctctctat tcggttgtct    180
tcttctttgg taagcaaaag aagaagaaga cgtaatagag aaactgaaag aaaaaaggga    240
caaaaatcaa gctgtcccgg catttactct ttgttttcta ccagctttct ctacttttgt    300
ctgatcttcc gaaatgtaac cgcttcactc atat                                334

<210> SEQ ID NO 6
<211> LENGTH: 25
<212> TYPE: DNA
<213> ORGANISM: Lycopersicon esculentum

<400> SEQUENCE: 6
gaatcatgaa tgctccaccg catga                                           25

<210> SEQ ID NO 7
<211> LENGTH: 25
<212> TYPE: DNA
<213> ORGANISM: Lycopersicon esculentum

<400> SEQUENCE: 7
tgctgagaag acacattaag gtaac                                           25

<210> SEQ ID NO 8
<211> LENGTH: 25
<212> TYPE: DNA
<213> ORGANISM: Lycopersicon esculentum

<400> SEQUENCE: 8
taacattgca ttacaacact ggaca                                           25

<210> SEQ ID NO 9
<211> LENGTH: 25
<212> TYPE: DNA
<213> ORGANISM: Lycopersicon esculentum

<400> SEQUENCE: 9
catgaatgct ccaccgcatg acgta                                           25

<210> SEQ ID NO 10
<211> LENGTH: 20
<212> TYPE: DNA
<213> ORGANISM: Lycopersicon esculentum

<400> SEQUENCE: 10
ttcactggca cgccctaaca                                                 20
```

```
<210> SEQ ID NO 11
<211> LENGTH: 28
<212> TYPE: DNA
<213> ORGANISM: Lycopersicon esculentum

<400> SEQUENCE: 11
tggtaccatc tccctgcat atgccaac                                           28

<210> SEQ ID NO 12
<211> LENGTH: 32
<212> TYPE: DNA
<213> ORGANISM: Lycopersicon esculentum

<400> SEQUENCE: 12
ggagaaaccg ataaagaaga acgggaagaa ga                                     32

<210> SEQ ID NO 13
<211> LENGTH: 34
<212> TYPE: DNA
<213> ORGANISM: Lycopersicon esculentum

<400> SEQUENCE: 13
aatcattgtt tttgttgaat ttgttaaaat gggt                                   34

<210> SEQ ID NO 14
<211> LENGTH: 32
<212> TYPE: DNA
<213> ORGANISM: Lycopersicon esculentum

<400> SEQUENCE: 14
caggaacact ggacattaac taaatatagt ac                                     32

<210> SEQ ID NO 15
<211> LENGTH: 28
<212> TYPE: DNA
<213> ORGANISM: Lycopersicon esculentum

<400> SEQUENCE: 15
aggccacggc agaaccgtcc tctctgca                                          28

<210> SEQ ID NO 16
<211> LENGTH: 28
<212> TYPE: DNA
<213> ORGANISM: Lycopersicon esculentum

<400> SEQUENCE: 16
agtccaagat cacgccatcc tccctaca                                          28

<210> SEQ ID NO 17
<211> LENGTH: 24
<212> TYPE: DNA
<213> ORGANISM: Lycopersicon esculentum

<400> SEQUENCE: 17
gattgctttc ttgtgtgctt catc                                              24

<210> SEQ ID NO 18
<211> LENGTH: 24
<212> TYPE: DNA
<213> ORGANISM: Lycopersicon esculentum

<400> SEQUENCE: 18
ggtaacttga tattgtccaa attc                                              24
```

```
<210> SEQ ID NO 19
<211> LENGTH: 24
<212> TYPE: DNA
<213> ORGANISM: Lycopersicon esculentum

<400> SEQUENCE: 19
gtgccaacgc acaattttat tagc                                          24

<210> SEQ ID NO 20
<211> LENGTH: 25
<212> TYPE: DNA
<213> ORGANISM: Lycopersicon esculentum

<400> SEQUENCE: 20
ccatggacaa ataaaacttc atgtc                                         25

<210> SEQ ID NO 21
<211> LENGTH: 43
<212> TYPE: DNA
<213> ORGANISM: Lycopersicon esculentum

<400> SEQUENCE: 21
tttggatcca atcattgttt ttgttgaatt tgttaaaatg ggt                     43

<210> SEQ ID NO 22
<211> LENGTH: 24
<212> TYPE: DNA
<213> ORGANISM: Lycopersicon esculentum

<400> SEQUENCE: 22
taagagctcc aacattaatc atgt                                          24

<210> SEQ ID NO 23
<211> LENGTH: 24
<212> TYPE: DNA
<213> ORGANISM: Lycopersicon esculentum

<400> SEQUENCE: 23
acatgattaa tgttggagct ctta                                          24

<210> SEQ ID NO 24
<211> LENGTH: 40
<212> TYPE: DNA
<213> ORGANISM: Lycopersicon esculentum

<400> SEQUENCE: 24
ttgagctcca ggaacactgg acattaacta aatatagtac                         40

<210> SEQ ID NO 25
<211> LENGTH: 207
<212> TYPE: PRT
<213> ORGANISM: Lycopersicon esculentum

<400> SEQUENCE: 25
```

Ile Asp Pro Ser Thr Gln Lys Phe Pro Cys Cys Leu Val Trp Thr Pro
 1               5                  10                  15

Leu Pro Val Ile Ser Trp Leu Ala Pro Phe Val Gly His Val Gly Ile
            20                  25                  30

Cys Arg Glu Asp Gly Thr Ile Val Asp Phe Ser Gly Asp Ser Met Ile
        35                  40                  45

His Phe Gly Gln Leu Phe Tyr Gly Thr Val Ala Lys Tyr Tyr Gln Val
    50                  55                  60

```
Asp Arg Gln Gln Cys Cys Phe Ala Arg Asn Phe Gly His Thr Cys
 65                  70                  75                  80

Arg Lys Gly Tyr Glu His Val Val Phe Gly Thr Ala Val Ser Trp Asp
                 85                  90                  95

Asp Ala Val Gln Leu Phe Arg Arg Thr Phe Glu Asn Arg Asn Phe Lys
            100                 105                 110

Val Phe Ser Cys Asn Gly His Ser Phe Ala Ala Asp Cys Leu Asn Leu
        115                 120                 125

Leu Ser Phe Arg Gly Ser Met Arg Trp Asn Met Ile Asn Val Gly Ala
130                 135                 140

Leu Ile Met Phe Glu Gly Lys Trp Val Ser Arg Trp Ser Met Leu Arg
145                 150                 155                 160

Ser Phe Leu Pro Phe Ile Gly Ile Leu Cys Phe Gly Tyr Leu Met Ile
                165                 170                 175

Gly Trp Met Phe Pro Ile Gly Leu Leu Ser Phe Val Ile Gly Thr Phe
            180                 185                 190

Gly Trp Tyr Val Met Ile Cys Tyr Cys Cys Lys Ile Glu Asp Asp
        195                 200                 205

<210> SEQ ID NO 26
<211> LENGTH: 207
<212> TYPE: PRT
<213> ORGANISM: Lycopersicon esculentum

<400> SEQUENCE: 26

Ile Asn Gly Glu Asn Ala Lys Phe Pro Cys Cys Leu Val Trp Thr Pro
 1               5                  10                  15

Leu Pro Val Val Ser Trp Leu Ala Pro Phe Ile Gly His Val His Ile
            20                  25                  30

Cys Arg Glu Asp Gly Ser Ala Val Ala Phe Ser Gly Ser Asn Phe Ile
        35                  40                  45

Asn Ile Asp Asp Phe Ala Leu Gly Ser Val Ala Lys Tyr Leu Gln Leu
    50                  55                  60

Asp Arg Lys Gln Cys Cys Phe Pro Arg Asn Leu Ala Ala His Thr Cys
 65                  70                  75                  80

Lys His Gly Tyr Lys His Thr Glu Phe Gly Ser Ala Ile Thr Trp Asp
                 85                  90                  95

Asp Ala Ile Gln Ser Ser Val Arg His Phe Glu His Lys Ser Tyr Asn
            100                 105                 110

Ile Phe Thr Cys Asn Ser Tyr Ser Phe Val Ala Asn Cys Leu Asn Arg
        115                 120                 125

Leu Cys Tyr Gly Gly Ser Met Asp Trp Asn Met Ile Asn Val Gly Ala
130                 135                 140

Leu Leu Leu Phe Lys Gly His Trp Val Asp Asn Met Ser Ile Leu Arg
145                 150                 155                 160

Ser Phe Ser Pro Phe Met Leu Val Val Cys Phe Gly Ile Phe Met Val
                165                 170                 175

Gly Trp Pro Phe Met Val Ala Leu Leu Ala Phe Ser Leu Leu Leu Leu
            180                 185                 190

Ala Trp Phe Ile Phe Gly Thr Tyr Cys Leu Lys Asn Leu Leu Asp
        195                 200                 205

<210> SEQ ID NO 27
<211> LENGTH: 207
<212> TYPE: PRT
<213> ORGANISM: Lycopersicon esculentum
```

<400> SEQUENCE: 27

```
Ile Asp Thr Lys Lys Ser Lys Phe Pro Cys Cys Ile Val Trp Thr Pro
  1               5                  10                  15

Leu Pro Val Val Ser Trp Leu Ala Pro Phe Ile Gly His Ile Gly Leu
             20                  25                  30

Cys Arg Glu Asp Gly Val Ile Leu Asp Phe Ala Gly Ser Asn Phe Ile
         35                  40                  45

Asn Val Asp Asp Phe Ala Phe Gly Pro Pro Ala Arg Tyr Leu Gln Leu
     50                  55                  60

Asp Arg Thr Lys Cys Cys Leu Pro Pro Asn Met Gly Gly His Thr Cys
 65                  70                  75                  80

Lys Tyr Gly Phe Lys His Thr Asp Phe Gly Thr Ala Arg Thr Trp Asp
                 85                  90                  95

Asn Ala Leu Ser Ser Thr Arg Ser Phe Glu His Lys Thr Tyr Asn
            100                 105                 110

Ile Phe Thr Cys Asn Cys His Ser Phe Val Ala Asn Cys Leu Asn Arg
        115                 120                 125

Leu Cys Tyr Gly Gly Ser Met Glu Trp Asn Met Val Asn Val Ala Ile
    130                 135                 140

Leu Leu Met Ile Lys Gly Lys Trp Ile Asn Gly Ser Ser Val Val Arg
145                 150                 155                 160

Ser Phe Leu Pro Cys Ala Val Val Thr Ser Leu Gly Val Val Leu Val
                165                 170                 175

Gly Trp Pro Phe Leu Ile Gly Leu Ser Ser Phe Ser Leu Leu Leu Phe
            180                 185                 190

Ala Trp Phe Ile Ile Ala Thr Tyr Cys Phe Lys Asn Ile Ile Thr
        195                 200                 205
```

<210> SEQ ID NO 28
<211> LENGTH: 207
<212> TYPE: PRT
<213> ORGANISM: Lycopersicon esculentum
<400> SEQUENCE: 28

```
Ile Asp Pro Lys Arg Ala Arg Phe Pro Cys Cys Ile Val Trp Thr Pro
  1               5                  10                  15

Leu Pro Ile Val Ser Trp Leu Ala Pro Tyr Ile Gly His Ala Gly Ile
             20                  25                  30

Cys Arg Glu Asp Gly Thr Val Leu Asp Phe Ala Gly Ser Asn Leu Val
         35                  40                  45

Ser Met Asp Asn Phe Ala Tyr Gly Ser Ile Ala Arg Tyr Leu Gln Leu
     50                  55                  60

Asp Arg Lys Lys Cys Cys Phe Pro Val Asn Leu Ala Thr His Val Cys
 65                  70                  75                  80

Glu Arg Ser Tyr Lys His Ala Glu Ala Gly Thr Ala Ile Ser Trp Asp
                 85                  90                  95

Asp Ala Leu Gln Leu Gly Met Arg Ser Phe Gly His Lys Phe Tyr Asn
            100                 105                 110

Leu Phe Thr Cys Asn Cys Tyr Ser Phe Val Ala Asn Cys Leu Asn Arg
        115                 120                 125

Leu Ala Tyr Asn Gly Ser Val Lys Trp Asn Val Ile Asn Val Ala Ala
    130                 135                 140

Leu Val Trp Leu Arg Gly Gln Trp Val Asp Lys Met Ser Val Val Arg
145                 150                 155                 160

Ser Phe Phe Pro Phe Leu Thr Val Thr Cys Val Gly Ile Leu Met Ala
```

```
                        165                 170                 175
Gly Trp Pro Phe Leu Ile Gly Met Ala Ala Phe Ser Ser Leu Leu Ile
                180                 185                 190
Gly Trp Phe Val Phe Ala Val Tyr Cys Met Lys Asp Leu Val Cys
            195                 200                 205

<210> SEQ ID NO 29
<211> LENGTH: 207
<212> TYPE: PRT
<213> ORGANISM: Lycopersicon esculentum

<400> SEQUENCE: 29

Val Asp Gln Lys Gly Thr Arg Phe Pro Cys Cys Ile Val Trp Thr Pro
1               5                   10                  15
Leu Pro Val Val Ser Trp Leu Ala Pro Tyr Ile Gly His Val Gly Ile
            20                  25                  30
Ala Arg Glu Asp Gly Thr Val Met Asp Phe Ala Gly Ser Asn Phe Val
        35                  40                  45
Ser Val Asp Asp Leu Ala Tyr Gly Ser Ala Ala Arg Tyr Leu Gln Leu
    50                  55                  60
Asp Arg Arg Lys Cys Cys Phe Pro Ala Asn Leu Ala Ala His Val Cys
65                  70                  75                  80
Ala Arg Ser Tyr Glu His Ser Glu Ala Gly Thr Ala Ile Ser Trp Asp
                85                  90                  95
Asp Ala Leu Gln Ser Gly Ala Arg Arg Phe Glu His Lys Cys Tyr Asn
            100                 105                 110
Leu Phe Thr Cys Asn Ser His Ser Phe Val Ala Ser Cys Leu Asn Arg
        115                 120                 125
Leu Ala Tyr Gly Gly Ser Val Gly Trp Asn Val Ile Asn Leu Ala Ala
    130                 135                 140
Leu Val Trp Leu Arg Gly Arg Trp Leu Gly Lys Met Ala Val Val Arg
145                 150                 155                 160
Ser Leu Leu Pro Phe Ala Ala Val Ala Cys Val Gly Val Leu Met Ala
                165                 170                 175
Gly Trp Ser Phe Leu Ile Ser Met Ala Ala Phe Ser Ser Leu Leu Leu
            180                 185                 190
Gly Trp Phe Val Leu Gly Val Tyr Cys Phe Lys Gly Leu Val Cys
        195                 200                 205

<210> SEQ ID NO 30
<211> LENGTH: 208
<212> TYPE: PRT
<213> ORGANISM: Lycopersicon esculentum

<400> SEQUENCE: 30

Ile Asp Pro Lys Arg Asp Arg Phe Pro Cys Cys Ile Val Trp Ser Pro
1               5                   10                  15
Leu Pro Val Leu Ser Trp Phe Ile Pro Phe Ile Gly His Ile Gly Ile
            20                  25                  30
Cys Arg Glu Asp Gly Val Ile Leu Asp Phe Ala Gly Pro Asn Phe Val
        35                  40                  45
Ser Val Asp Asn Phe Thr Phe Gly Ala Pro Thr Cys Tyr Phe Gln Leu
    50                  55                  60
Ser Arg Glu Gln Cys Cys Cys Leu Ser Pro Tyr Ser Ala Glu Pro Thr
65                  70                  75                  80
Gly Glu Tyr Val Glu Asn His Asp Glu Ser Gly Gly Asn Val Asp Thr
                85                  90                  95
```

Trp Glu Ser Ala Ile Arg Lys Ser Ile Gln Glu Phe Gln His Gln Ser
            100                 105                 110

Tyr Ser Ile Phe Thr Cys Asn Cys His Ser Phe Val Ala Asn Gly Leu
        115                 120                 125

Asn Arg Leu Gly Phe Gln Ser Gly Gly Trp Asn Val Asn Leu Ala
    130                 135                 140

Ile Phe Ile Phe Leu Lys Gly Arg Trp Val Asn Arg Thr Ala Met Val
145                 150                 155                 160

Lys Thr Tyr Leu Pro Pro Leu Val Val Leu Gly Leu Gly Leu Ile Phe
                165                 170                 175

Gly Gly Gly Thr Phe Leu Thr Tyr Leu Leu Ile Phe Met Phe Val Leu
                180                 185                 190

Ile Gly Trp Phe Leu Leu Gly Thr Tyr Cys Phe Lys Lys Leu Ile His
                195                 200                 205

<210> SEQ ID NO 31
<211> LENGTH: 208
<212> TYPE: PRT
<213> ORGANISM: Lycopersicon esculentum

<400> SEQUENCE: 31

Leu Asp Pro Arg Arg Ala Arg Phe Pro Cys Cys Ile Val Trp Thr Pro
1               5                   10                  15

Leu Pro Val Ile Ser Trp Leu Ile Pro Phe Val Gly His Ile Gly Ile
                20                  25                  30

Cys Arg Glu Asp Gly Val Ile Leu Asp Phe Ala Gly Pro Asn Phe Val
            35                  40                  45

Cys Val Asp Asn Phe Ala Phe Gly Ala Val Thr Arg Tyr Ile Gln Ile
        50                  55                  60

Ser Lys Glu Lys Cys Cys Ile Ser Pro His His Pro Ala Pro Tyr Arg
65                  70                  75                  80

Arg Glu Asn Gly Arg Gly Gln Asp Glu Thr Glu Asp Ile Leu Thr
                85                  90                  95

Trp Asp Asp Ala Leu Arg Lys Ser Thr Gln Glu Phe Gln His Arg Ser
            100                 105                 110

Tyr Asn Leu Phe Thr Cys Asn Cys His Ser Phe Val Ala Asn Asn Leu
        115                 120                 125

Asn Arg Leu Gly Phe Tyr Asp Gly Gly Trp Asn Val Val Asn Leu Ala
    130                 135                 140

Ala Leu Ile Phe Leu Lys Gly Arg Trp Val Ser Thr Thr Ser Met Ile
145                 150                 155                 160

Lys Ser Phe Leu Pro Phe Ala Ile Val Ser Ala Leu Gly Leu Phe Phe
                165                 170                 175

Gly Gly Leu Thr Phe Leu Thr Phe Leu Ala Phe Phe Thr Phe Leu Leu
                180                 185                 190

Val Gly Trp Phe Leu Leu Gly Thr Tyr Cys Phe Lys Asn Leu Ile His
                195                 200                 205

<210> SEQ ID NO 32
<211> LENGTH: 209
<212> TYPE: PRT
<213> ORGANISM: Lycopersicon esculentum

<400> SEQUENCE: 32

Ile Asp Pro Lys Arg Asp Arg Phe Pro Cys Cys Ile Val Trp Thr Pro
1               5                   10                  15

```
Leu Pro Phe Ile Ser Trp Leu Val Pro Phe Ile Gly His Val Gly Ile
            20                  25                  30

Cys Arg Glu Asp Gly Val Ile Leu Asp Phe Ala Gly Pro Asn Phe Val
        35                  40                  45

Cys Val Asp Asn Phe Ala Phe Gly Ala Val Ser Arg Tyr Ile Gln Ile
    50                  55                  60

Asn Lys Glu Met Glu Ser Ser Arg Ser Ser Ser Gly Met Phe Asn
65                  70                  75                  80

Gly Glu Arg Arg Tyr Glu Gln Glu Asp Ser His Glu Lys Glu Pro
                85                  90                  95

Thr Trp Asp Asp Ala Leu Arg Lys Ser Thr Gln Glu Tyr Gln His His
            100                 105                 110

Ser Tyr Asn Ile Leu Thr Cys Asn Cys His Ser Phe Val Ala Asn Asn
        115                 120                 125

Leu Asn Arg Leu Ser Ile Lys Ser Gly Gly Trp Asn Val Val Asn Leu
    130                 135                 140

Ala Thr Leu Val Leu Phe Lys Gly Arg Trp Val Asn Lys Thr Ala Ile
145                 150                 155                 160

Val Lys Ser Leu Leu Pro Pro Leu Thr Val Tyr Thr Ile Gly Ile Leu
                165                 170                 175

Leu Gly Gly Trp Thr Phe Ile Ala Ser Cys Ser Ile Leu Val Val Leu
            180                 185                 190

Leu Thr Gly Trp Phe Ile Ile Gly Thr Tyr Cys Phe Lys Lys Leu Ile
        195                 200                 205

Gln

<210> SEQ ID NO 33
<211> LENGTH: 193
<212> TYPE: PRT
<213> ORGANISM: Lycopersicon esculentum

<400> SEQUENCE: 33

Ile Asp Pro Arg Arg Ala Arg Phe Pro Cys Cys Ile Val Trp Thr Pro
1               5                   10                  15

Leu Pro Leu Ile Ser Trp Leu Ile Pro Phe Ile Gly His Ile Gly Ile
            20                  25                  30

Cys Arg Glu Asp Gly Val Ile Leu Asp Phe Ala Gly Pro Asn Phe Val
        35                  40                  45

Ser Val Asp Asn Phe Ala Phe Gly Ala Val Ala Arg Tyr Ile Gln Val
    50                  55                  60

Asn Ser Asp Glu Cys Tyr Lys Leu Leu Glu Pro Glu Gly Ala Ser Thr
65                  70                  75                  80

Trp Asp Asp Ala Leu Arg Lys Gly Val Gln Glu Phe Gln His Arg Gly
                85                  90                  95

Tyr Ser Leu Phe Thr Cys Asn Cys His Ser Phe Val Asn Asn Leu
            100                 105                 110

Asn Arg Leu Phe Tyr Ser Gly His Asp Lys Trp Asn Val Val Ser Leu
        115                 120                 125

Ala Ala Val Met Phe Leu Arg Gly Arg Trp Val Ser Thr Ala Ser Val
    130                 135                 140

Val Lys Thr Phe Phe Pro Phe Ala Leu Val Ile Thr Ile Gly Thr Leu
145                 150                 155                 160

Leu Gly Gly Ala Thr Phe Leu Ile Gly Leu Leu Ala Phe Ala Ala Val
                165                 170                 175

Met Thr Gly Trp Phe Leu Val Gly Thr Tyr Cys Ile Lys Ser Leu Val
```

Glu

<210> SEQ ID NO 34
<211> LENGTH: 164
<212> TYPE: PRT
<213> ORGANISM: Lycopersicon esculentum

<400> SEQUENCE: 34

```
Met Asp Val Glu Arg Ser Arg Phe Pro Tyr Cys Val Val Trp Thr Pro
1               5                   10                  15
Ile Pro Val Leu Thr Trp Phe Phe Pro Ile Ile Gly His Met Gly Ile
                20                  25                  30
Cys Thr Ser Ala Gly Val Ile Arg Asp Phe Ala Gly Pro Tyr Phe Val
            35                  40                  45
Ser Glu Asp Asn Met Ala Phe Gly Lys Pro Ala Lys Phe Trp Lys Leu
    50                  55                  60
Asp Pro Gly Gln Val Tyr Ala Ser Gly Pro Asn Ala Trp Asp Thr Ala
65                  70                  75                  80
Val His Asp Ala Ser Glu Glu Tyr Lys His Arg Met His Asn Leu Cys
                85                  90                  95
Cys Asp Asn Cys His Ser His Val Ala Leu Ala Leu Asn Leu Met Arg
            100                 105                 110
Tyr Asn Asn Ser Thr Asn Trp Asn Met Val Thr Leu Cys Cys Phe Cys
        115                 120                 125
Leu Ile Tyr Gly Lys Tyr Val Ser Val Gly Ala Phe Val Lys Thr Trp
    130                 135                 140
Leu Pro Phe Val Leu Leu Leu Gly Ile Ile Leu Thr Val Ser Leu Val
145                 150                 155                 160
Phe Asn Leu Arg
```

<210> SEQ ID NO 35
<211> LENGTH: 164
<212> TYPE: PRT
<213> ORGANISM: Lycopersicon esculentum

<400> SEQUENCE: 35

```
Met Asp Val Glu Arg Ser Arg Phe Pro Tyr Cys Val Val Trp Thr Pro
1               5                   10                  15
Ile Pro Val Leu Thr Trp Phe Phe Pro Ile Ile Gly His Met Gly Ile
                20                  25                  30
Cys Thr Ser Thr Gly Val Ile Arg Asp Phe Ala Gly Pro Tyr Phe Val
            35                  40                  45
Ser Glu Asp Asn Met Ala Phe Gly Lys Pro Ala Lys Tyr Trp Lys Leu
    50                  55                  60
Asp Pro Ala Gln Val Tyr Ala Ser Gly Pro Asn Ala Trp Asp Thr Ala
65                  70                  75                  80
Val His Asp Ala Ser Glu Glu Tyr Lys His Arg Met His Asn Leu Cys
                85                  90                  95
Cys Asp Asn Cys His Ser His Val Ala Leu Ala Leu Asn Leu Met Arg
            100                 105                 110
Tyr Asn Asn Ser Thr Asn Trp Asn Met Val Thr Leu Cys Cys Phe Cys
        115                 120                 125
Leu Leu Tyr Gly Lys Tyr Val Ser Val Gly Ala Phe Val Lys Thr Trp
    130                 135                 140
Leu Pro Phe Ile Leu Leu Leu Gly Ile Ile Leu Thr Val Ser Leu Val
```

```
             145                 150                 155                 160

Phe Asn Leu Arg

<210> SEQ ID NO 36
<211> LENGTH: 160
<212> TYPE: PRT
<213> ORGANISM: Lycopersicon esculentum

<400> SEQUENCE: 36

Ile Asn Val Lys Asp Gln Arg Phe Pro Tyr Cys Ile Val Trp Thr Pro
  1               5                  10                  15

Ile Pro Val Leu Thr Trp Leu Met Pro Met Ile Gly His Met Gly Ile
             20                  25                  30

Cys Thr Ser Ser Gly Val Ile Arg Asp Phe Ala Gly Pro Tyr Phe Val
         35                  40                  45

Ser Glu Asp Asn Met Ala Phe Gly Arg Pro Thr Arg Tyr Ile Arg Leu
     50                  55                  60

His Pro Lys His Met Val Gly Gly Ser Tyr Ala Trp Asp Glu Ala Val
 65                  70                  75                  80

Ser Lys Ala Ser Val Leu Tyr Gly Thr Arg Ile His Asn Ile Phe Cys
                 85                  90                  95

Asp Asn Cys His Ser His Val Ala Thr Ala Leu Ile Tyr Met Arg Tyr
            100                 105                 110

Tyr Asp Ser Thr Ala Trp Asn Met Ile Ile Leu Ser Met Trp Leu Phe
        115                 120                 125

Val Cys Gly Arg Tyr Val Gly Ile Gly Gly Phe Ile Lys Thr Trp Leu
    130                 135                 140

Pro Phe Ala Ile Leu Leu Ser Ile Phe Thr Ile Leu Gly Ile Tyr Phe
145                 150                 155                 160

<210> SEQ ID NO 37
<211> LENGTH: 154
<212> TYPE: PRT
<213> ORGANISM: Lycopersicon esculentum

<400> SEQUENCE: 37

Arg Tyr Pro Tyr Cys Ile Val Trp Thr Pro Ile Pro Cys Leu Thr Trp
  1               5                  10                  15

Phe Phe Pro Phe Ile Gly His Met Gly Ile Ala Asn Ser Arg Gly Ile
             20                  25                  30

Ile Arg Asp Phe Ala Gly Ser Tyr Tyr Val Ala Glu Asp Asp Met Gly
         35                  40                  45

Phe Gly Trp Pro Thr Arg Tyr Trp Gln Leu Gly Pro Glu Lys Val Glu
     50                  55                  60

Gly Gly Ala Glu Val Phe Asp Arg Ala Val Gln Asp Ala Ser Asp Thr
 65                  70                  75                  80

Tyr Lys Thr Arg Thr His Asn Leu Ile Cys Asp Asn Cys His Ser His
                 85                  90                  95

Val Ala Leu Ala Leu Asn Lys Met Arg Tyr Asp Glu Arg Glu Asp Trp
            100                 105                 110

Asn Met Ile Asn Leu Ala Trp Tyr Ser Leu Thr Lys Gly Ser Phe Val
        115                 120                 125

Arg Asn Thr Asp Met Leu Ala Gln Tyr Leu Pro Phe Val Ile Val
    130                 135                 140

Phe Ile Phe Val Ala Leu Trp Ala Phe Leu
145                 150
```

RIPENING INHIBITION IN THE TOMATO *GREEN-RIPE* MUTANT RESULTS FROM ECTOPIC EXPRESSION OF A NOVEL PROTEIN WHICH DISRUPTS ETHYLENE SIGNAL TRANSDUCTION

BACKGROUND OF THE INVENTION

1. Field of the Invention

This invention relates to a gene, the GR gene, cloned from tomato mutants, a construct containing the gene and its promoter, a vector and method of transforming plants utilizing the construct and vector, and plants transformed with the gene construct.

2. Description of the Relevant Art

The ripe phenotype is the summation of biochemical and physiological changes occurring at the terminal stage of fruit development rendering the organ edible and desirable to seed dispersing animals and valuable to humans as an important food source and an agricultural commodity. Ripening changes, although variable among species, generally include modification of cell wall ultrastructure and texture, conversion of starch to sugars, increased susceptibility to post-harvest pathogens, alterations in pigment biosynthesis/accumulation, and heightened levels of flavor and aromatic volatiles (Hobson and Grierson. 1993. In: *Biochemistry of Fruit Ripening*, Seymour et al., eds., Chapman and Hall, London, pp. 405-442). Several of these ripening attributes translate to decreased shelf life and high input harvest, shipping and storage practices, particularly via changes in firmness and the overall decrease in resistance to microbial infection of ripe fruit. Currently acceptable techniques for minimizing the consequences of undesirable ripening characteristics include premature harvest, controlled atmosphere storage, pesticide application, and chemically induced ripening to synchronize the time of maturation. Unfortunately, added production, shipping and processing expenses, in addition to reduced fruit quality, are often the consequence of these practices, challenging the competitiveness, quality, and long-term sustainability of current levels of crop production.

The regulatory pathways that control fruit ripening are not fully understood although comparative analysis indicates that there is an emerging theme of conservation. For example, in silico mining of EST collections has revealed conservation of transcription factors that show ripening-related expression in tomato, a climacteric fruit, and grape, a non-climacteric fruit (Fei et al. 2004. *Plant J.* 40: 47-59). In addition, the RIN gene that encodes a MADS box protein essential for ripening in tomato (Vrebalov et al. 2002.) is functionally conserved in melon and strawberry (Binzel et al., unpublished data; Manning et al., unpublished data). In climacteric fruit that includes tomato, banana, apples and stone fruits, there is a conserved increase in respiration and ethylene synthesis that occurs at the onset of ripening (Lelievre et al. 1997. *Physiol. Plant.* 101: 727-739). The importance of ethylene for the co-ordination and completion of ripening in climacteric fruit has, been demonstrated through treatment of fruit with inhibitors of ethylene synthesis and action (Hobson et al. 1984. *J. Plant Physiol.* 116: 21-30; Yang, S. F. 1985. *Hortscience* 20: 41-45) and in transgenic and mutant plants blocked in their ability to produce or respond to ethylene (Klee et al. 1991. *Plant Cell* 3: 1187-1194; Oeller et al. 1991. *Science* 254: 437-439; Picton et al. 1993. *Plant J.* 3: 469-481; Wilkinson et al. 1995. *Science* 270: 1807-1809)

Altered ethylene responsiveness in plant tissues affects normal development and can compromise the plants ability to respond to environmental stimuli (Bleeker et al. 1988. *Science* 241: 1086-1089; Guzman and Ecker. 1990. *Plant Cell* 2: 513-524; Lanahan et al. 1994. *Plant Cell* 6: 521-530; Wang et al. 2002. *Plant Cell* 14: S131-S151). The mechanisms by which the ethylene signal is perceived and transduced to mediate phenotypic changes is not fully understood although many elegant studies exploiting the triple response screen in *Arabidopsis* have led to the identification of critical components of this signaling pathway (Guo and Ecker. 2004. *Curr. Opin. Plant Biol.* 7: 40-49).

The ethylene signal is initially perceived by a family of receptors that share homology to bacterial two-component regulators (Chang et al. 1993. *Science* 262: 539-544; Hua et al. 1995. *Science* 269: 1712-1714; Hua et al. 1998. *Plant Cell* 10: 1321-1332; Sakai et al. 1998. *Proc. Natl. Acad. Sci. USA* 95: 5812-5817). Loss of function analysis indicates that the receptors act in a semi-redundant manner to negatively regulate ethylene responses (Hua and Meyerowitz. 1998. *Cell* 94: 261-271). At least two receptors interact with Constitutive Triple Response 1 (CTR1), a serine threonine MAPKKK that acts as a negative regulator of the pathway (Kieber et al. 1993. *Cell* 72: 427-441; Clark et al. 1998. *Proc. Natl. Acad. Sci. USA* 95: 5401-5406; Gao et al. 2003. *J. Biol. Chem.* 278: 34725-34732). An integral membrane protein, EIN2, with homology to the NRAMP family of metal ion transporters acts downstream of the receptors and CTR1 (Roman et al. 1995. *Genetics* 139:1393-1409). The biochemical function of EIN2 remains unknown but genetic studies have indicated that all ethylene responses described to date are transduced through this signaling intermediate (Hall and Bleecker. 2003. *Plant Cell* 15: 2032-2041). A family of transcription factors encoded by EIN3 and EIL (EIN3-like) act downstream of EIN2 (Chao et al. 1997. *Cell* 89: 1133-1144; Solano et al. 1998. *Genes Dev.* 12: 3703-3714). Homodimers of EIN3, EIL1 and EIL2 bind to a defined target site in the promoter region of the transcription factor, Ethylene Response Factor 1 (ERF-1) (Solano et al., supra). ERF1 is part of a large multigene family of transcription factors and is important in the regulation of downstream ethylene responsive genes via binding to the "GCC" box promoter element (Ohme-Takagi et al. 2000. *Plant Cell Physiol.* 41: 1187-1192; Fujimoto et al. 2000. *Plant Cell* 12: 393-404). Ethylene responses are regulated at the level of EIN3 via ubiquitin/proteasome-dependent proteolysis mediated by the F-box proteins, EBF1 and EBF2 (Guo and Ecker. 2003. *Cell* 115: 667-677; Potuschak et al. 2003. *Cell* 115: 679-689).

The importance of ethylene in regulating traits of agronomic importance, particularly fruit ripening and floral senescence, has driven research on the identification and functional characterization of components of the ethylene signaling pathway in crop species (Klee, H.-J. 2004. *Plant Physiol.* 135: 660-667; Adams-Phillips et al. 2004a. *Trends in Plant Science* 9: 331-338). Studies utilizing tomato and petunia have been at the forefront of this comparative analysis and have revealed structural and functional conservation of the ethylene signaling pathway (Adams-Phillips et al. 2004b. *Plant Mol. Biol.* 54: 387-404; Leclercq et al. 2002. *Plant Physiol.* 130: 1132-1142; Shibuya et al. 2004. *Plant Physiol.* 136: 2900-2912; Tieman et al. 2001. *Plant J.* 26: 47-58; Tieman et al. 2000. *Proc. Natl. Acad. Sci. USA* 97: 5663-5668; Wilkinson et al. 1995. *Science* 270: 1807-1809). Interestingly there is an expansion of the gene families encoding the receptors and CTR components in tomato and other crop plants adding a further layer of complexity to the ethylene response pathway (Klee, H.-J., supra; Adams-Phillips et al. 2004a, b, supra). Expression studies of these genes further suggest tissue-specific transcription of some receptors (Tieman and Klee. 1999. *Plant Physiol.* 120: 165-172), though no ethylene signaling genes that function exclusively or even predominantly in fruit or related floral tissues have been described to date.

Thus, the plant hormone ethylene has profound effects on fruit ripening and senescence, conditions that ultimately result in a deterioration of quality in a wide range of horticultural crops. Having greater understanding of how ethylene regulates ripening and senescence provides us with tools for improving agricultural production as well as products with enhanced nutritional and flavor attributes.

This invention concerns the cloning of a novel gene, GR, at the Gr/Nr-2 locus that is able to differentially regulate tissue-specific ethylene responses in tomato with the most dramatic effect observed during inhibition of fruit ripening.

SUMMARY OF THE INVENTION

We have cloned a novel gene at the Gr/Nr-2 locus and determined that expression of the GR gene results in the inhibition of fruit ripening and the differential regulation of tissue-specific ethylene responses in tomato.

In accordance with this discovery, it is an object of the invention to provide an isolated nucleic acid construct containing a DNA sequence which encodes the GR protein, the expression of said protein being involved in the regulation of ripening in climacteric fruit and senescence and abscission in flowers.

It is a further object of the invention to provide a vector which comprises a construct which is capable of expressing the GR gene.

It is a still further object of the invention to provide a host cell comprising the vector capable of expressing the GR gene.

It is an additional object of the invention to provide transgenic plants, plant cells, and seeds containing the nucleic acid construct.

It is another object of the invention to provide a method of manipulating fruit ripening in plants by stably transforming a plant with an isolated nucleotide molecule capable of regulating ethylene responses, operably linked with a promoter capable of driving expression of a gene in a plant cell.

It is another object of the invention to provide a method of manipulating senescence and abscission in plants by stably transforming a plant with an isolated nucleotide molecule capable of regulating ethylene responses, operably linked with a promoter capable of driving expression of a gene in a plant cell.

It is yet another object of the invention to provide a method of transforming the GR gene into a plant by administering a vector, wherein said vector comprises an effective amount of a nucleic acid construct, a DNA sequence which is capable of transforming the GR gene into a plant, resulting in the inhibition of fruit ripening and flower senescence and abscission in said plant.

It is yet another object of the invention to provide plants, plant cells, and plant parts, that have been transformed by the GR gene-containing construct of the invention and that are thereby capable of modulating fruit ripening and flower senescence and abscission when compared to plants of the same species which have not been transformed.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A shows the genetic map of the Nr-2 locus flanked by the RFLP markers TG260 and TG245 based on a total of 1810 F2 individuals. With the exception of the RFLP markers TG38, TG245, TG260 and TG333, markers are derived from the ends of BAC and cosmid clones. The number of recombinant individuals between adjacent markers is shown. BAC and cosmid clones isolated with either TG333 (93D5) or 93R (26A21, 237H16, 151L6), are represented by horizontal bars. Clones 931D5, 26A21, 237H16 were isolated from an *S. cheesmaniae* BAC library and 151L6 was isolated from an *S. lycopersicum* cosmid library. The approximate size of each clone, as determined by pulse field gel electrophoresis, is indicated in kb. The four candidate genes at the Nr-2 locus are labeled with their corresponding EST identifier (Solanaceous Genomics Network. SGN data overview. [online]. Boyce Thompson Institute for Plant Research, Room 221, Tower Road, Ithaca. NY 14853, USA. [retrieved on 2005-00-00]. Retrieved from the Internet: <URL: www.sgn.cornell.edu). Arrows indicate the predicted direction of transcription. FIG. 1B shows the predicted genomic structure corresponding to the EST clone cLPT12O9. Relative positions of primers used for RT-PCR (C1, C2, R) and amplification of genomic DNA (G1, G2) are shown. FIG. 1C shows the RT-PCR amplification of cLPT12O9 from wild type Ailsa Craig (AC) and mutant (Gr and Nr-2) genotypes. cDNA was synthesized from 500 ng of total RNA extracted from a pool of mixed fruit stages. An equal amount of cDNA template was used for PCR amplification using either C1 and R primers or C2 and R primers. Amplification using gene-specific primers corresponding to SGN-U239539 was used as an equal loading control. FIG. 1D shows the PCR amplification of genomic DNA using the primers G1 and G2 and the identification of a deletion at the Gr and Nr-2 loci. The amplicon from wild type (AC) DNA is approximately 1400 bp. M refers to a DNA ladder.

FIG. 2A depicts segregation of ripening inhibition in T1 progeny of four independent transgenic individuals (lines 4, 6, 7 and 8) expressing the GR cDNA under the control of the CaMV 35S promoter. Normal ripening fruit (−) have segregated out the transgene whereas non-ripening fruit (+) have retained the transgene. Wild type (AC) and Gr fruit of identical age are shown for comparison. FIG. 2B reflects GR expression in fruit samples shown in FIG. 2A. Total RNA (20 µg) extracted from normal ripening fruit was hybridized to a $^{32}$P-labelled GR probe. The filter was stripped and re-probed with an 18S rRNA probe as an equal loading control. FIG. 2C shows petal retention on developing fruits of multiple CaMV35S:GR transgenic lines. FIG. 2D shows the frequency of ethylene-induced floral abscission. Cut flower stalks of wild type (AC), Gr and two homozygous independent CaMV35S:GR transgenic lines (4-20 and 6-14) were placed in water and sealed in a gas tight container with 2 µl/l ethylene. The percentage of abscised flowers was monitored after 72 h. The mean of three independent experiments with a total of at least 134 flowers is presented. Vertical bars represent SE.

FIG. 3C depicts GR expression in hypocotyls of etiolated seedlings. Total RNA (20 µg) extracted from the genotypes described in FIG. 3A was hybridized to a $^{32}$P-labelled GR probe. The filter was stripped and reprobed with an 18S rRNA probe as an equal loading control.

FIG. 5 shows the amino acid alignment of GR (SEQ ID NO:25), i.e., AA 36-233 of SEQ ID NO:4 and homologous proteins [GRL1 (SEQ ID NO:26); At 2G26070 (SEQ ID NO:27); Rice 1 (SEQ ID NO:28); Rice 2 (SEQ ID NO:29); GRL2 (SEQ ID NO: 30); Grape (SEQ ID NO:31); AT3G51040 (SEQ ID NO:32); Rice 3 (SEQ ID NO:33); Mouse (SEQ ID NO:34); Human (SEQ ID NO:35); *Drosophila* (SEQ ID NO:36); *C. elegans* (SEQ ID NO:37)]. Protein alignments based on full length amino acid sequences were performed using ClustalW. Conserved amino acids are indicated by shaded squares.

FIG. 7A shows GR expression during fruit ripening in wild type (AC) and Gr. Developmental stages 1 through 5 are defined in Example 1. GR expression in fruit in response to ethylene is shown in FIG. 7B. Mature green fruit treated were treated with (+) or without (−) 20 µl/l of ethylene for 16 h. GR expression during tomato seed development is shown in FIG. 7C. RNA was extracted from seed of wild type tomato fruit at the immature green (2), mature green (3) and red-ripe (4) stages of development. RNA extracted from Gr mature green fruit pericarp tissue was included as a positive control (1).

DETAILED DESCRIPTION OF THE INVENTION

Figure 1:
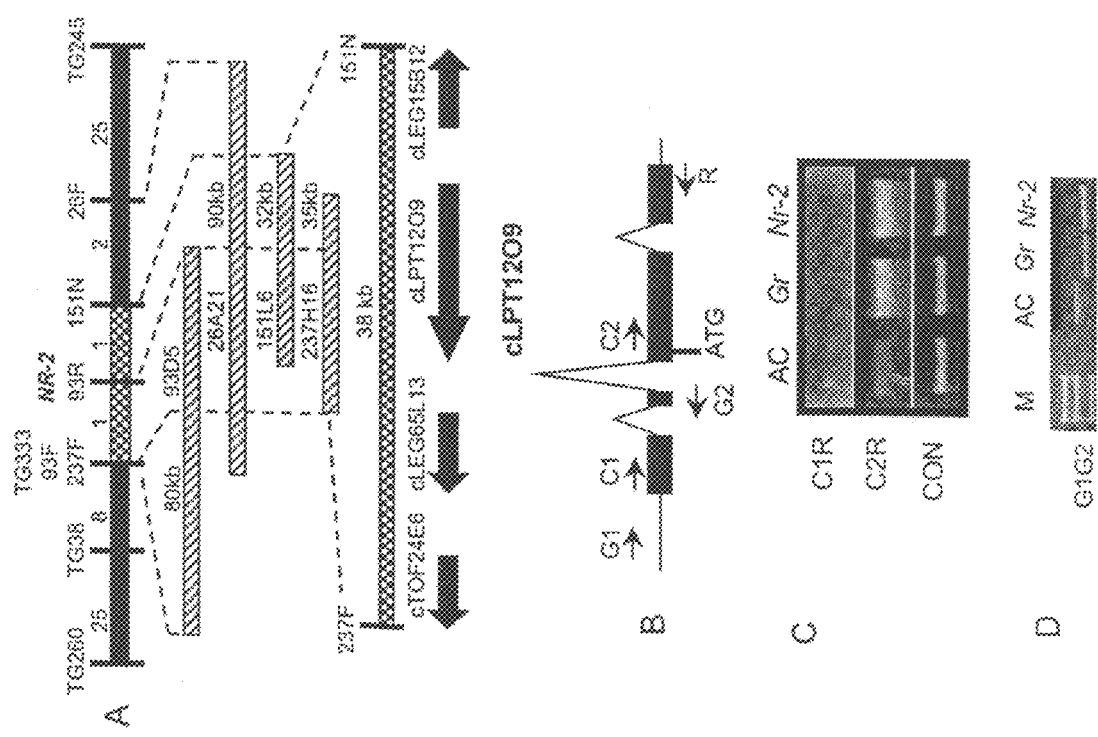
FIGS. 1A-1D depict the structure of the Gr and Nr-2 loci.

We have recently reported that severe inhibition of fruit ripening in the Green-ripe (Gr) and Never-ripe 2 (Nr-2) ripening mutants of tomato is the result of ethylene insensitivity (Barry et al. 2005. *Plant Physiol.* 138: 267-275, incorporated herein by reference). Gr and Nr-2 plants also display subdued ethylene responses associated with floral senescence, abscission and root elongation during the triple response. However, ethylene-mediated inhibition of hypocotyl elongation and petiole epinasty are normal in mutant plants suggesting that these loci affect only a subset of ethylene responses in tomato with the strongest phenotypes seen only in fruit (Barry et al., supra).

Tomato monogenic mutants with inhibited or modified ripening characteristics have been powerful tools for defining our current knowledge of factors that regulate ripening and fruit quality. A combination of positional cloning and candidate gene analysis has led to the isolation of the genes responsible for conferring the Never-ripe (Nr), ripening-inhibitor (rin), non-ripening (nor), high pigment-1 (hp-1) and high pigment-2 (hp-2) mutations (Wilkinson et al. 1995, supra; Mustilli et al. 1999. Plant Cell 11: 145-157; Vrebalov et al., supra; Giovannoni, J. J. 2004. *Plant Cell* 16: S170-S180; Liu et al. 2004. *Proc. Natl. Acad. Sci. USA* 101: 9897-9902). This invention concerns the isolation of the GR gene, a gene involved in the differential regulation of tissue-specific ethylene responses in tomato, the most dramatic effect being observed during inhibition of fruit ripening, but inhibition of senescence and abscission also being seen; the cloning and functional analysis of the GR gene in mutant and wild type tomato plants; and the transformation of an additional plant, the tomato plant, with nucleic acid encoding the GR protein. Using the compositions and methods of the invention, plant cells are genetically manipulated resulting in differential regulation of fruit ripening in plant cells and tissues. The nucleic acid molecules, constructs and vectors of the invention and the methods of using them can be utilized to inhibit fruit ripening and differentially regulate other tissue-specific ethylene responses in important food crops, e.g., delaying floral senescence and abscission and regulating root elongation. The GR gene represents a regulatory gene serving as a controlling switch of the ethylene response in specific tissues of the plant.

Positional cloning of the GR/NR-2 locus revealed the presence of an identical 334 by deletion in Gr/Gr and Nr-2/Nr-2 genotypes indicating that these two mutations are allelic. The deletion resides in the 5'-flanking region of a gene encoding an evolutionary conserved putative membrane protein of unknown function that we now refer to solely as the GR gene. Molecular analysis revealed that the Gr/Nr-2 deletion results in ectopic expression of GR in mutant fruit, a phenomenon consistent with a dominant gain of function mutation. Constitutive over-expression of GR under the control of the CaMV35S promoter in transgenic plants recreates the Gr mutant phenotypes, indicating that the positional cloning experiments correctly identified the target gene. However, constitutive over-expression of GR does not lead to reduced ethylene sensitivity throughout the plant, as hypocotyl responses to ethylene are normal. The ability of GR to selectively inhibit ethylene responses suggests that tissue-specific signaling mechanisms operate in tomato. Given that this effect is brought about by a dominant gain of function mutation, the components of the ethylene signaling pathway in tomato must differ between hypocotyls and petioles as compared to the other tissues examined, i.e., fruit, petals, abscission zones and roots. GR encodes a novel protein of unknown biochemical function that has not previously been associated with control of ripening and ethylene sensitivity in plants. GR belongs to a family of putative membrane localized proteins that are conserved in eukaryotes.

The phenotypic similarity between Gr and Nr-2 mutants coupled with their close physical proximity within the genome led us to speculate that they may represent allelic mutations (Barry et al., supra). The presence of an identical deletion in both mutants (FIG. 1D) was unexpected given that both arose spontaneously (Kerr, E. A. 1982. *Rpt Tomato Genetics Coop* 32: 33; Kerr, E. A. 1958. *Rpt Tomato Genetics*

Coop 8: 22). To exclude any possibility that our seed stocks were contaminated, we confirmed the presence of the deletion in the accessions LA2453 and LA2455 (data not shown). These accessions are homozygous for the Gr and Nr-2 mutation respectively, possess distinct plant and fruit morphology and were used as donors in the generation of our near isogenic lines (NILs) and F2 mapping populations (Barry et al., supra). To our knowledge no other accessions carrying these mutations exist and therefore two possibilities remain: 1) an identical spontaneous mutation arose independently on two occasions or 2) Nr-2 is the result of a pollen or seed contaminant derived from Gr. We are proposing to name the gene at the Gr/Nr-2 locus GREEN RIPE (GR) after the accession LA2453 that was first described (Kerr, E. A. 1958, supra). This will avoid any confusion regarding comparisons between Never-ripe and Never ripe-2, the former encoding an ethylene receptor in tomato (Wilkinson et al. 1995, supra).

Figure 2:
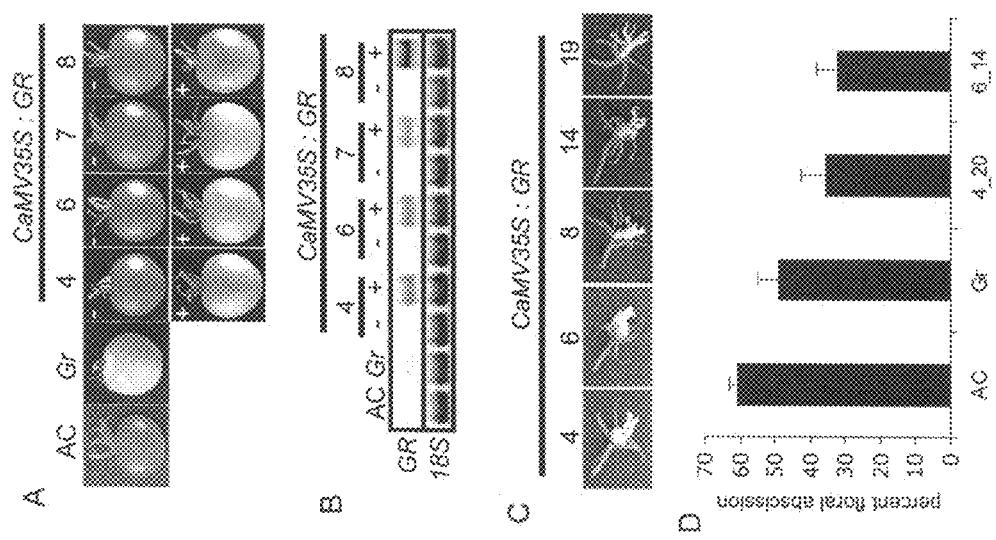
FIGS. 2A-D depict CaMV35S:GR expression.
Figure 3:
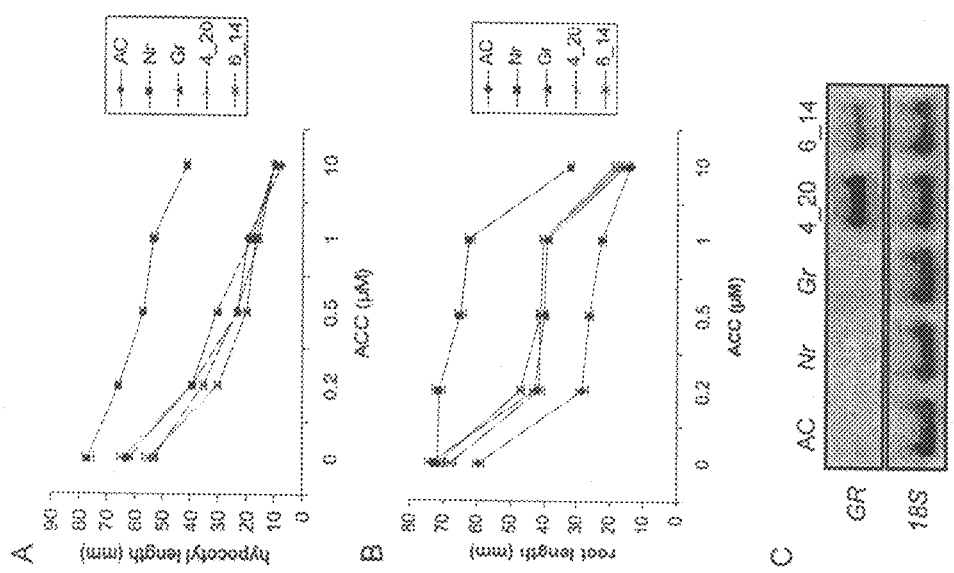
FIGS. 3A-C illustrate the seedling triple response phenotype in CaMV35S:GR transgenic lines and depict the growth of seeds of five different genotypes: wild type (AC), Nr, Gr and the CaMV35S:GR lines 4-20 and 6-14. Seeds were surface sterilized and sown on 0.8% water agar containing 1-aminocyclopropane-1-carboxylic acid (ACC) at the indicated concentrations. Following growth in the dark for eight days at 25° C.; hypocotyl (FIG. 3A) and root lengths (FIG. 3B) were determined. Each data point is the result of measurements of at least 31 seedlings. Vertical bars represent SE.

The Gr mutant displays reduced ethylene responsiveness in fruit, floral senescence and abscission and root elongation but not in hypocotyls or petioles (Barry et al., supra). The data indicate that these phenotypes are caused by ectopic expression of GR in mutant tissues resulting from a deletion of 5"-UTR and upstream regulatory sequences (FIGS. 1C, 2, 3). We hypothesized that CaMV35S:GR expression might lead to reduced ethylene responsiveness throughout the plant resulting in reduced ethylene sensitivity in dark grown hypocotyls. However, our data do not support this hypothesis despite high accumulation of GR transcripts in transgenic lines (FIGS. 3A, C). These data suggest that GR can modulate ethylene responses in a tissue-specific manner; and, given that this effect is brought about by a dominant gain of function mutation, indicates that components of the ethylene signaling pathway differ in tomato between hypocotyls and the other tissues examined in this study, i.e., fruit, petals, abscission zones and roots. The factors responsible for these differences remain unknown; however, it is possible that GR may function to disrupt ethylene signaling from specific receptors. Analysis of the expression patterns of the different ethylene receptor genes suggests that different tissues likely contain different pools of receptor proteins (Klee et al., supra). For example, LeETR4 and LeETR5 are predominantly expressed in floral and fruit tissues and very low or no expression is detected in etiolated hypocotyls (Tieman and Klee, supra). A correlation therefore exists between the expression of these receptor isoforms and GR function. Identification of GR provides a tool to assess apparent tissue-specific ethylene signal transduction.

Tissue-specific perturbation of ethylene responses has been previously documented in several *Arabidopsis* mutants, namely hookless 1 (hls1), ethylene-insensitive root 1 (eir1), enhanced ethylene response 1 (eer1), weak ethylene insensitive 2 and 3 (wei2, wei3) (Guzman and Ecker, supra; Roman et al., supra; Larsen and Chang. 2001. *Plant Physiol.* 125: 1061-1073; Alonso et al. 2003. Proc. Natl. Acad. Sci. USA 100: 2992-2997). These mutants display ethylene insensitivity in a single aspect of seedling morphology. Molecular characterization has revealed that all function to regulate synthesis, transport or responsiveness to auxin (Lehman et al. 1996. *Cell* 85: 183-194; Li et al. 2004. *Developmental Cell* 7: 193-204; Luschnig et al. 1998. *Genes Dev.* 12: 2175-2187; Stepanova et al. 2005. *Plant Cell* 17: 2230-2242) or, in the case of eer1 which encodes the protein phosphatase 2A, a regulatory subunit, RCN1 (Larsen and Cancel. 2003. *Plant J.* 34: 709-718), to participate in the function of multiple hormonal signaling pathways (Kwak et al. 2002. *Plant Cell* 14: 2849-2861; Garbers et al. 1996. *EMBO J.* 15: 2115-2124). The specificity of the Gr mutant phenotype differs from that, of the *Arabidopsis* tissue-specific mutants in that ethylene responsiveness was reduced notably, though only moderately, in the majority of the tissues examined though with a dramatic impact on fruit ripening. At present we cannot rule out that GR participates in the signaling of multiple hormone response pathways.

Figure 4:
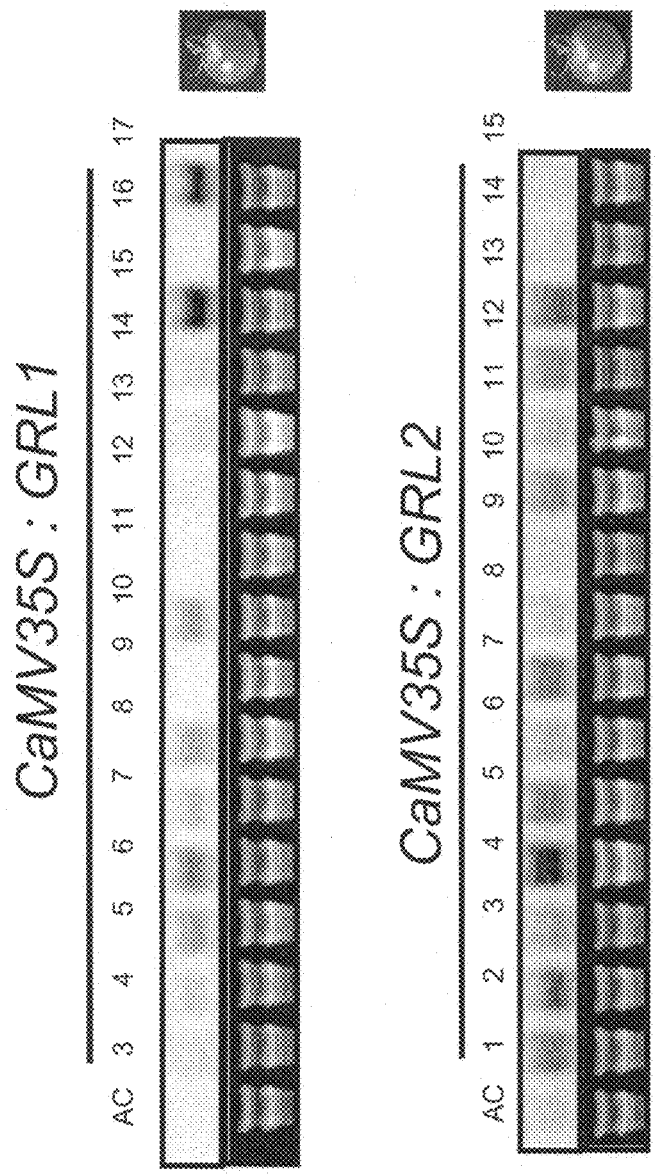
FIG. 4 shows GRL1 and GRL2 expression in leaves of multiple lines of independent primary transformants expressing either a CaMV35S:GRL1 (Lines 3-17) or CaMV35S: GRL2 (Lines 1-15) transgene when GRL1 and GRL2 overexpression lines were generated.

As GR confers a dominant gain of function mutation, a fundamental question regarding GR function is whether the protein is an integral component of the ethylene signaling pathway or a component of a second pathway (possibly hormonal) that is able to selectively inhibit ethylene responses. One hypothesis to explain GR function is that deregulated expression of GR in mutant fruit is able to inhibit the normal functioning of GRL1 or GRL2 via a currently undetermined mechanism that may involve competing for binding partners or disrupting protein complexes. This hypothesis assumes that either or both GRL1 and GRL2 normally function as positive regulators of ethylene signaling in tomato. Consistent with this hypothesis, primary transformants over-expressing GRL1 and GRL2 do not display ethylene insensitive phenotypes as do the GR over-expression lines described here. For example fruit from CaMV35S:GRL1 and CaMV35S:GRL2 lines ripen normally and show no signs of delayed petal senescence despite high transgene expression (FIG. 4; C. Barry and J. J. Giovannoni, unpublished data). A second hypothesis to explain GR function is that the plant controls levels of GR to selectively repress ethylene signaling in tissues where this may be detrimental to plant or cell survival. The levels of GR expression are low or undetectable in all tissues that we examined with the exception of developing seeds. It is possible that GR expression may be increased in developing seeds to inhibit ethylene signaling and protect the developing embryo. The function of ethylene in developing tomato seeds is unclear, but studies in *Arabidopsis*, petunia and maize implicate ethylene in regulating the levels of multiple hormones and ABA signaling to control dormancy, seed weight and cell death in the endosperm respectively (Beaudoin et al. 2000. *Plant Cell* 12: 1103-1115; Chiwocha et al. 2005. *Plant J.* 42: 35-48; Clevenger et al. 2004. *J. Am. Soc. Hortic. Sci.* 129: 401-406; Young and Gallie. 2000. *Plant Mol.* 44: 283-301).

Figure 5:
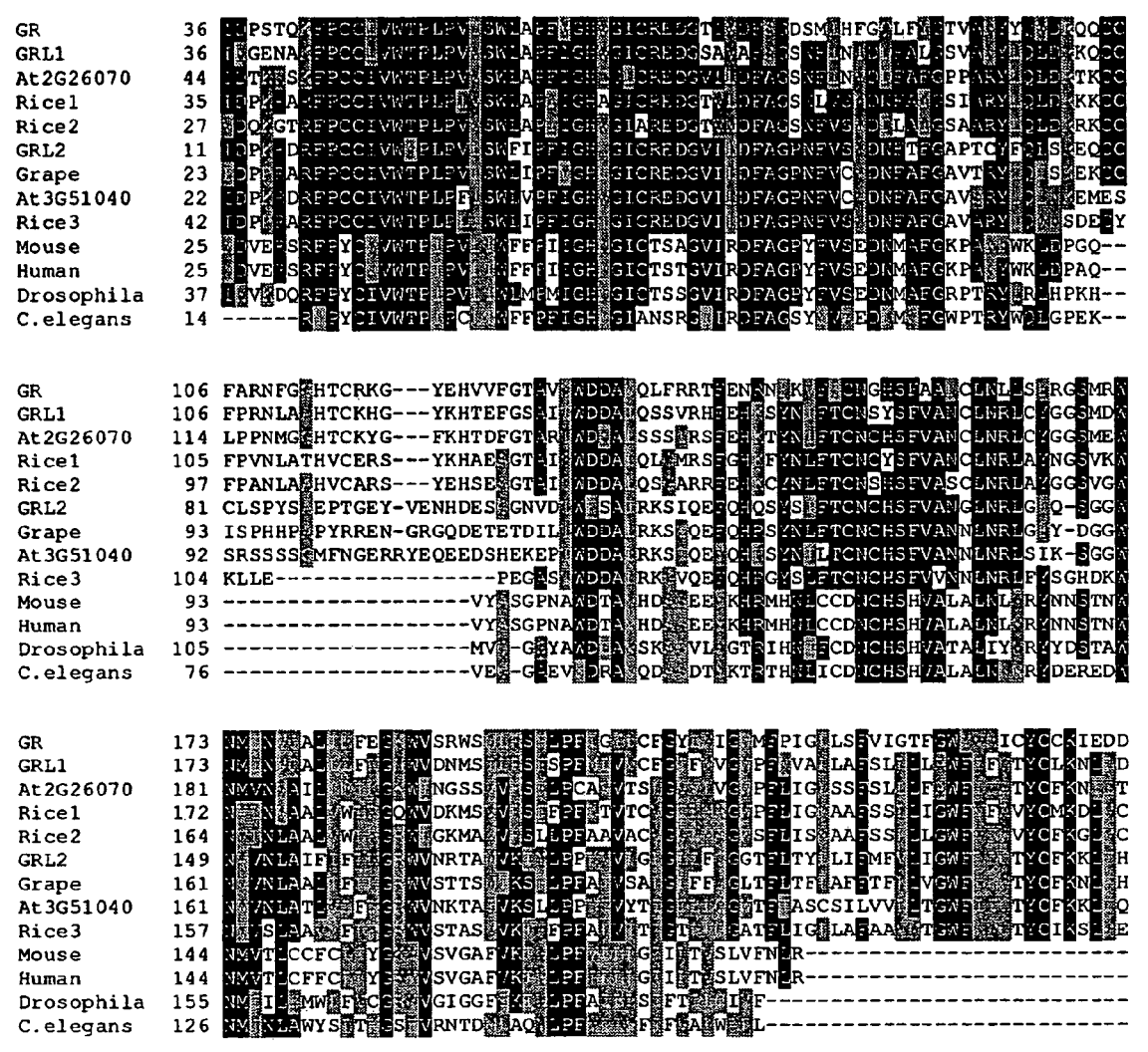
Figure 6:
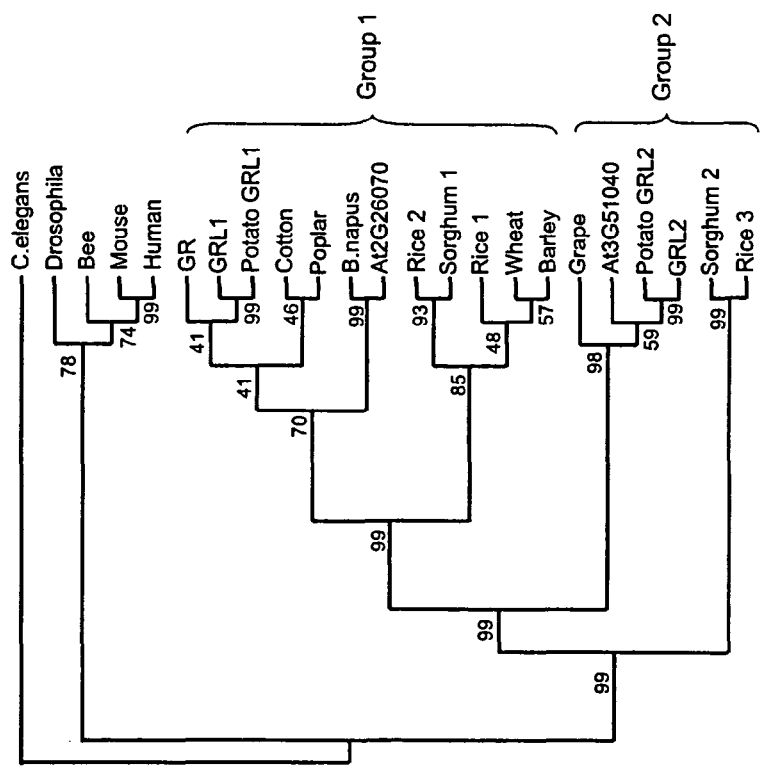
FIG. 6 depicts the phylogenetic analysis of GR related proteins. Protein alignments based on full-length amino acid sequences were performed using ClustalX. Phylogenetic relationships between the proteins were analyzed using the PHYLIP 3.5C suite of programs (http://evolution.genetics.washington.edu/phylip.html). The maximum parsimony, distance matrix and likelihood methods of the Protpars and Seqboot programs were utilized to estimate phylogenies. A non-rooted phylogenetic tree was generated using Consense and the Treeview package using the *C. elegans* protein as the out-group. The single most parsimonious tree obtained in a heuristic search following 100 random sequence addition replicates is shown. Bootstrap percentage supports are indicated at the branches of the tree.

Comparison of the deduced amino acid sequence of GR with various sequence repositories identified a number of homologous proteins in a range of eukaryotes (FIGS. 5 and 6). The biochemical function of this family remains a mystery, but all possess a conserved domain of unknown function (DUF778). GR is currently the only member of this family to which a mutant phenotype has been assigned. The tomato members of the GR family are diverse in the composition of their primary sequence. For example the two most closely related proteins, GR and GRL1, share only 52 percent amino acid identity. In addition GR, but not other family members, contains an MXCXXC at the carboxy terminus of the protein and an MXXXM motif within one of the predicted transmembrane spanning domains. These motifs have been shown to participate in the binding of copper ions in the Abel protein of yeast and the copper transport activity of the high affinity copper uptake proteins (Ctr proteins) of human and yeast respectively (Pufahl et al. 1997. *Science* 278: 853-856; Puig et al. 2002. *J. Biol. Chem.* 277: 26021-26030). The significance of these motifs requires further investigation, but metal ion homeostasis is fundamental for signaling in the ethylene response pathway. The receptors contain copper that mediates ethylene binding (Rodriguez et al. 1999. *Science* 283: 996-998). Furthermore, mutations at the response to antagonist 1 (ran1) locus which encodes a conserved copper transporting P-type ATPase disrupt ethylene signaling (Woeste and Keiber. 2000. *Plant Cell* 12: 443-455; Hirayama et al. 1999. *Cell* 97: 383-393), the ein2 locus encodes a protein of unknown function that shares homology with the NRAMP family of metal ion transporters (Alonso et al., supra) and pharmacological studies implicate calcium in transduction of the ethylene signal (Raz and Fluhr. 1992. *Plant Cell* 4: 1123-1130).

Control of ethylene responsiveness in crop plants is of commercial importance to reduce senescence, over-ripening and post-harvest deterioration of fruit, vegetable and floral crops. Previous research has led to the generation of transgenic horticultural crops with altered ethylene responsiveness to counteract the negative impacts of ethylene on ripening and floral senescence (Wilkinson et al. 1997. *Nat. Biotechnol.* 15: 444-447; Cui et al. 2004. *Plant Science (Oxford)* 167: 253-258; Bovy et al. 1999. *Molecular Breeding* 5: 301-308). These studies have successfully achieved their aims, but subsequent evaluation of horticultural performance has revealed that constitutive ethylene-insensitivity mediated by a dominant gain of function receptor mutation has deleterious effects on seed germination, seedling vigor and adventitious rooting in tomato and petunia (Clevenger et al., supra; Clark et al. 1999. *Plant Physiol.* 121: 53-59; Gubrium et al. 2000. *J. Am. Soc. Hortic. Sci.* 125: 277-281). The Gr mutant and the CaMV35S:GR transgene have a range of phenotypic penetrance in different tissues (i.e., a strong influence in fruit, moderate impact on floral senescence and abscission, a weak effect on root growth and no discernable changes in hypocotyl or shoot growth; FIGS. 2 and 3). This differential mediation of ethylene responsiveness by GR may be useful for reducing the impact of the less desirable consequences of ethylene on tissues such as ripe fruit whilst maintaining normal plant vigor.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" or "recombinant construct" refers to a nucleic acid sequence encoding a protein, here the GR protein, operably linked to a promoter and/or other regulatory elements or sequences.

As used herein, the term "express" or "expression" is defined to mean transcription alone. The regulatory elements are operably linked to the coding sequence of the GR gene such that the regulatory element is capable of controlling expression of GR gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to GR polypeptide that is substantially free of other proteins, lipids, carbohydrates or other materials with which it is naturally associated. One skilled in the art can purify GR using standard techniques for protein purification. The purity of the GR polypeptide can also be determined by amino-terminal amino acid sequence analysis.

The invention includes functional GR polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of GR polypeptide", refers to all fragments of GR that retain GR activity and function in the ethylene response pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of GR in the ethylene response pathway can be utilized in bioassays to identify functional fragments of GR polypeptide or related polypeptides.

Modifications of the GR primary amino acid sequence may result in further mutant or variant proteins having substantially equivalent activity to the GR polypeptides described herein. Such modifications may be deliberate, as by site-directed mutagenesis, or may occur by spontaneous changes in amino acid sequences where these changes produce modified polypeptides having substantially equivalent activity to the GR polypeptides. Any polypeptides produced by minor modifications of the GR primary amino acid sequence are included herein as long as the biological activity of GR is present; e.g., having a role in ethylene response pathways leading to inhibition of fruit ripening in plants.

A heterologous coding sequence refers to coding sequences which encode peptides or proteins, unrelated to, or, other than, the GR polypeptides provided above and which are not intrinsically found in the position provided in the chimeric gene construct.

Genes encoding a GR protein can be cloned using a variety of techniques according to the invention. The simplest procedure for the cloning of GR genes requires the cloning of genomic DNA from an organism identified as producing a GR protein, and the transfer of the cloned DNA on a suitable plasmid or vector to a host organism which does not produce the GR protein, followed by the identification of transformed hosts to which the ability to produce the GR protein has been conferred. The transforming GR-conferring DNA can be cleaved into smaller fragments and the smallest which maintains the GR-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a GR polypeptide and which hybridize under stringent conditions to the GR sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Sequence alignments and percent identity calculations were performed as described below in Example 2.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, tomato. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have GR-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the GR polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, GR activity as described herein. Such variants may result from, for example, genetic polymorphism or from human manipulation. Biologically active variants of a native GR protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired GR activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of GR protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The GR gene of the invention has been identified and cloned by using a map-based cloning strategy. The successful cloning of GR is a major step in our understanding of the regulatory mechanisms underlying differential regulation of the ethylene response and inhibition of fruit ripening in plants. Deciphering the mechanism by which this gene functions to result in the inhibition of fruit ripening will aid in devising new strategies and/or control points for improving the consequences of undesirable ripening characteristics in crops.

EXAMPLES

Having now generally described this invention, the same will be better understood by reference to certain specific examples, which are included herein only to further illustrate the invention and are not intended to limit the scope of the invention as defined by the claims.

Example 1

Plant Materials

All mutant lines and mapping populations used in this study have been previously described (Barry et al., supra). Briefly, homozygous lines carrying the Gr/Gr and Nr-2/Nr-2 mutations and the wild tomato species *Solanum cheesmaniae* (accession nos. LA2453, LA2455, and LA483, respectively) were obtained from the Tomato Genetics Resource Center, UC Davis. Homozygous Nr/Nr seed and the parental cultivar AC (nr/nr) were originally obtained from the Glasshouse Crops Research Institute (Littlehampton, Sussex, UK). Plants were grown in peat-based compost supplemented with fertilizer in greenhouses equipped with heating and cooling systems and supplemental lighting at Cornell University campus in Ithaca, N.Y. Fruit were harvested at five developmental stages (termed 1-5). For the AC cultivar, these were mature green (stage1), breaker (stage 2), breaker+3 d (stage 3), breaker+7 d (stage 4), and breaker+10 d (stage 5). To account for the more protracted ripening observed for the Gr and Nr2 NILs, fruit were harvested as follows based upon changes in color: mature green (stage 1), early breaker, defined as changes in internal color only (stage 2), breaker (stage 3), yellow (stage 4), and orange (stage 5). Stage 5 fruits were taken at around 60 d postanthesis (DPA). For comparison, stage 5 AC control fruit are approximately 42 DPA.

Experiments on dark grown seedlings were performed as follows. Surface sterilized seeds were sown on 1% water agar supplemented with ACC at 0, 0.2, 0.5, 1, and 10 µM and incubated in the dark for 7 d at 25° C. Ethylene treatment of light grown plants and mature green fruits was accomplished by sealing fruit in airtight chambers and injecting ethylene to a final concentration of 20 µl/l for 16 h. Experiments to evaluate the triple response phenotype in dark grown tomato seedlings and floral abscission were performed in the same way with the exception that responses of seedlings were measured at 8 days after sowing and flower responses were monitored for up to 72 h.

Example 2

Nucleic Acid Analysis

Genomic DNA isolation and genetic mapping were performed as previously described (Barry et al., supra). Briefly, genomic DNA was extracted from fresh meristematic leaves using a microprep isolation protocol modified from Fulton et al. (1995). Approximately six meristematic leaves were placed into a 2-mL screw-cap tube and kept on ice. Samples were homogenized in 290 µL of extraction buffer (0.35 M sorbitol, 0.1 M Tris-base, 5 mM EDTA, pH 7.5, containing 3.8 mg/mL sodium bisulfite) in a Savant FP120 Fast Prep machine. A total of 290 µL nuclear lysis buffer (0.2 M Tris-HCl, pH 8, 0.05 M EDTA, pH 8, 2 M NaCl, 2% (w/v) hexadecyl-trimethyl-ammonium bromide) and 140 µL 5% sodium lauryl sarcosine were added and the samples vortexed and incubated for 40 min at 65° C. A total of 700 µL of chloroform/octanol (24:1) was added and the samples were vortexed and centrifuged at 8,000 rpm for 15 min. The supernatant was transferred to a 1.5-mL microfuge tube and the DNA precipitated using 540 µL of cold isopropanol. DNA was pelleted by microcentrifugation for 10 min at 13,000 rpm and pellets were washed in 70% ethanol and airdried. DNA was resuspended by incubating pellets in 50 µL of sterile distilled water for 10 min at 65° C. Twenty microliters of DNA was digested in a total volume of 30 µL using restriction enzymes supplied by New England Biolabs (Beverly, Mass.) as per manufacturer's instructions. Digested DNA was fractionated through 1% agarose gels and "nicked" by UV light for 60 s. Gels were blotted in 0.4 N NaOH onto Hybond N+ membranes (Amersham Biosciences). Following transfer, membranes were baked at 80° C. for 2 h to fix the DNA to the membrane.

Details of tomato genetic maps and DNA markers can be accessed through the Solanaceous Genomics Network (SGN data overview. [online]. Boyce Thompson Institute for Plant Research, Room 221, Tower Road, Ithaca. NY 14853, USA,

[retrieved 2005-00-00]. Retrieved from the Internet: <URL: www.sgn.cornell.edu). A physical contig spanning the Gr locus was obtained via screening and characterization of ordered BAC and cosmid libraries derived from *Solanum lycopersicum* and *Solanum cheesmaniae* (Li et al., 2005. *Plant Cell* 17: 971-986; Budiman et al., 2000. *Genome Res.* 10: 129-136). BAC and cosmid ends were isolated by DNA sequencing and converted to RFLP or CAPS markers for further analysis. Restriction enzymes yielding polymorphisms between *S. lycopersicum* and *S. cheesmaniae* for given DNA probes are as follows; TG333: HaeIII, TG260: DraI, TG38: AccI, TG245: αTaqI, 26A21F: HpyCH41V, 151N: NlaIII, 93F: HaeIII, 93R: AluI, 237F: BfaI.

Total RNA was extracted from plant tissues and fractionated through 1% denaturing agarose gels as previously described (Barry et al., supra). Briefly, total RNA was extracted and fractionated through 1% denaturing agarose gels as described by Griffiths et al. (1999). Gels were blotted for 20 h in 10 mM sodium phosphate buffer onto Hybond N membranes (Amersham Biosciences, Piscataway, N.J.). Following transfer, membranes were baked at 80° C. for 2 h to fix the RNA to the membrane. RT-PCR amplification of GR from AC, Gr and Nr-2 genotypes was achieved through use of primers designed from the sequence of the EST clone cLPT12O9 (GenBank accession no. AW618118); C1: 5'-GAATCATGAATGCTCCACCGCATGA-3' (SEQ ID NO:6), C2: 5'-TGCTGAGAAGACACATTAAGGTAAC-3' (SEQ ID NO:7) and CR: 5'-TAACATTGC ATTACAA-CACTGGACA-3' (SEQ ID NO:8). cDNA was synthesized from 500 ng of total RNA extracted from a pool of mixed fruit stages using superscript II reverse transcriptase (Invitrogen). PCR amplification of genomic DNA spanning the deletion in Gr and Nr-2 was achieved using the primers G1: 5'-CATGAATGCTCCACCGCATGAC GTA-3' (SEQ ID NO:9) and G2: 5'-TTCACTGGCACGCCCTAACA-3'(SEQ ID NO:10).

DNA sequences were assembled using Sequencher™ version 4.2.2 (Genecodes). Amino acid sequences were deduced from cDNA clones using ORF Finder ([retrieved on 2005-00-00]. Retrieved from the Internet: <URL: www.ncbi.nlm.nih.gov/gorf/gorf.html). Prediction of transmembrane spanning domains was performed using the following programs: ConPredII (Arai et al. 2004. *Nucleic Acids Res.* 32: W390-W393), Thumbup (Zhou and Zhou. 2003. *Protein Science* 12: 1547-1555), HMMTOP 2.0 (Tusnady and Simon. 2001. *Bioinformatics (Oxford)* 17: 849-850), PHDhtm (Rost et al. 1996. *Protein Science* 5: 1704-1718), TMHMM ([retrieved on 2005-00-00]. Retrieved from the Internet: <URL: www.cbs.dtu.dk/services/TMHMM/) and TMPRED ([retrieved on 2005-00-00]. Retrieved from the Internet: <URL: www.ch.embnet.org/software/TMPRED forn.html). Deduced amino acid sequences of GR homologous proteins were obtained from GenBank, build three of the Solanaceous Genomics Network (SGN data overview. [online]. Boyce Thompson Institute for Plant Research, Room 221, Tower Road. Ithaca, N.Y. 14853, USA, [retrieved on 2005-00-00]. Retrieved from the Internet: <URL: www.sqn.cornell.edu) unigene set (SGN-U) and tentative consensus (TC) builds of the TIGR plant gene indices ([retrieved on 2005-00-00]. Retrieved from the Internet: <URL: www.tigr.org/tdb/tgi). Identifiers and GenBank accession numbers are as follows: Rice 1 (NP_916598), Rice 2 (AAV59409), Rice 3 (AAO37528), Human (NP_115501), Mouse (AAH37609), Honey Bee (XP_393764), *Drosophila* (NP_723362), *C. elegans* (AAF39886), Grape (TC40111) Sorghum 1 (TC94016), Sorghum 2 (TC97340), Barley (TC132972), Wheat (TC268045), *B. napus* (TC3567), Poplar (TC31211), Cotton (TC34712), Potato GRL2 (SGN-U276841). The *Arabidopsis thaliana* sequences, At2g26070 and At3g51040, are based on TAIR annotations ([retrieved on 2005-00-00]. Retrieved from the Internet: <URL: www.arabidopsis.org). Amino acid alignments were generated using either ClustalW or ClustalX and were decorated using the Boxshade server version 3.2.1 ([retrieved on 2005-00-00]. Retrieved from the Internet: <URL: www.ch.embnet.org). Phylogenetic trees were constructed using the PHYLIP version 3.5C suite of programs ([retrieved on 2005-00-00]. Retrieved from the Internet: <URL: evolution.genetics.washington.edu/phylip.html) and visualized using Treeview software.

Example 3

High Resolution Genetic and Physical Mapping of the Nr-2 and Gr Loci

Utilizing F2 populations segregating for normal and non-ripening fruit between *S. lycopersicum* (Gr/Gr)×*S. cheesmaniae* (gr/gr) and *S. lycopersicum* (Nr-21Nr-2)×*S. cheesmaniae* (nr-2/nr-2), we positioned the Gr and Nr-2 loci to overlapping regions of the long arm of tomato chromosome 1 with tight linkage to the RFLP marker TG333 (Barry at al., supra). The mapping resolution of each locus was increased to approximately 0.03 cM per recombination event by screening for recombinants between TG260 and TG245 in 1810 and 1856 F2 individuals segregating for Nr-2 and Or respectively. Simultaneously, TG333 was used to screen ordered BAC libraries derived from *Solanum lycopersicum* and *Solanum* cheesmaniae (Li et al., supra; Budiman et al., supra). A total of 13 BAC clones were recovered from these screens (data not shown). The ends from clone 93D5 (FIG. 1A) were isolated by direct sequencing and converted into the RFLP markers 93F and 93R. 93R was used as a probe to re-screen the BAC libraries in addition to a cosmid library derived from *Solanum lycopersicum*. Three additional clones 26A21, 237H16 and 151L6 were recovered. The ends of these clones were isolated by sequencing and converted to either RFLP or PCR based markers. Mapping of these markers indicated that the Nr-2 locus co-segregated with the marker 93R between the flanking loci 237F and 151N (FIG. 1A). Genetic mapping revealed that the Gr locus was positioned in the same interval (data not shown). Using a combination of BAC subclones and primer walking, this interval was sequenced and found to be 38 kb in length (SEQ ID NO:1), A BLAST search of the resulting sequence against build three of the Solanaceous Genomics Network unigene set (SGN data overview. [online]. Boyce Thompson Institute for Plant Research, Room 221, Tower Road. Ithaca, N.Y. 14853, USA, [retrieved on 2005-00-00]. Retrieved from the Internet: <URL: www.sgn.cornell.edu) revealed the presence of four predicted genes (FIG. 1A). ESTs were identified corresponding to each of these predicted genes and the longest corresponding cDNA clone from each of these unigenes was sequenced and aligned to the 38 kb genomic sequence. BLASTX searches of GenBank ([retrieved on 2005-00-00]. Retrieved from the Internet: <URL: www.ncbi.nlm.nih.gov/blast/) and the predicted proteins of *Arabidopsis* ([retrieved on 2005-00-00]. Retrieved from the Internet: <URL: www.arabidopsis.org) failed to reveal any additional genes residing in the 38 kb interval, suggesting that one or more of the four genes is altered in the Grand Nr-2 mutations.

Example 4

Structure of the Gr Gene

The 5' ends of cDNAs for GR were obtained by RACE using the BD Smamm RACE cDNA amplification kit (Clontech) and a primer, LPTGSPI: 5'-TGGTACCATCCT CCCT-GCATATGCCAAC-3' (SEQ ID NO:11), derived from cLPT12O9. Reactions were performed from normal gr/grand mutant Gr/Gr fruit RNA and RACE products were cloned into the pGEMT-Easy vector (Promega) and sequenced using vector primers. Full length cDNAs were subsequently amplified and cloned using the Zero Blunt® TOPO® PCR cloning kit (Invitrogen) using either GRACFLF: 5'-GGAGAAACCGAT AAAGAAGAACGGGAAGAAGA-3' (SEQ ID NO:12; gr/gr) or GRMUFLF: 5'-AATCAT TGTTTTTGT-TGAATTTGTTAAAATGGGT-3' (SEQ ID NO:13; Gr/Gr) in combination with the reverse primer GRACFLR: 5'-CAG-GAACACTGGACATTAACTAAATATAGT AC-3' (SEQ ID NO:14). RACE products of the 5' ends of GR-Like1 (GRL1; cDNA clone cLEG37H1 (GenBank accession no. BE461119)) and GR-Like2 (GRL2; cDNA clone cTOD5M16 (GenBank accession no. AW738161)) were obtained and characterized as described above using the primers LEG37H1GSP1: 5'-AGGCCACGGCAGAACCGT CCTCTCTGCA-3' (SEQ ID NO:15) and TOD5M16GSP1: 5'-AGTCCAAGATCACGCC ATCCTCCCTACA-3' (SEQ ID NO:16). Subsequently full-length cDNA clones for each were obtained using the primers GRL1FLF: 5'-GAT-TGCTTTCTTGTGTGCTTCATC-3' (SEQ ID NO:17), GRL1FLR: 5'-GGTAACTTGATATTGTCCAAATTC-3' (SEQ ID NO:18), GRL2FLF: 5'-GTGCCAACGCA-CAATTTTATTAGC-3' (SEQ ID NO:19) and GRL2FLR: 5'-CCATGGACAAATAAAACTTCATGTC-3' (SEQ ID NO:20) and cloned as described above.

Using primers designed to amplify full-length cDNA clones for each of the four candidate genes, RT-PCR analysis was performed on cDNA made from RNA of mixed stages of fruit development from three genotypes: AC (normal nearly isogenic control), Gr/Gr and Nr-2/Nr-2. Amplifying the predicted full length cDNA corresponding to cLPT12O9 (FIG. 1A) using the primers C1 and R (FIG. 1B, C) resulted in a faint band of the predicted size from the AC control template but no product was obtained following amplification from mutant samples. An independent RT-PCR reaction using a nested forward primer, C2 and the reverse primer, R, on the same RNA samples amplified a product of the predicted size from each genotype (FIG. 1B, C). Furthermore, a greater yield of PCR product was obtained from Gr and Nr-2 backgrounds implying that cLPT12O9 is more highly expressed than in the AC control sample. Lack of amplification of cLPT12O9 in RT-PCR experiments using the C1 primer with mutant-derived RNAs suggested the presence of a deletion covering, or a mutation at, the C1 primer site in the Gr and Nr-2 mutants. This was confirmed by PCR amplification from genomic DNA with primers G1 and G2 (FIG. 1D). A smaller fragment was amplified from Gr and Nr-2 mutant plants compared to that obtained from AC control plants. These fragments were cloned and sequenced and a single identical deletion of 334 by was confirmed in both Gr and Nr-2. Sequence alignment of the deletion to the S. lycopersicum genomic and full-length cDNA sequences, obtained by 5"RACE, revealed that the deletion results in the removal of 278 by of the first exon (within the 5' UTR) and 56 by of the putative promoter. However, the predicted protein-coding region of cLPT12O9 remains unchanged in both the Gr/Gr and Nr-2/Nr-2 genotypes. The deletion begins just 10 by downstream of the predicted TATA box suggesting that transcription initiation may be disrupted in Gr/Grand Nr-2/Nr-2 genotypes. This was confirmed by performing 5' RACE amplification on cDNA synthesized from wild type and Gr RNA which indicated that transcription is initiated at a point 372 by downstream of the wild-type site of transcription initiation of the normal, non-deleted genomic sequence, in mutant compared to wild type plants. Alignment of cDNA (SEQ ID NO:2) and genomic sequences from wild type plants reveals a 1451 base transcript derived from a genomic clone comprised of four exons separated by three introns. Two of the introns reside within the 5' UTR, the first being 101 by and the second being particularly large at 8880 bp. This gene structure is conserved in Gr although the first two introns are 1655 by and 7172 by respectively and occur at different positions to those in the wild type gene. Additionally the processed transcript size is 1235 bases in mutant plants. Again, the predicted coding region is not altered in mutant versus normal transcripts. An additional 694 bases upstream of the normal GR start of transcription was recovered through sequencing of the mutant allele and no additional sequence alterations were identified as compared the normal near isoline. This result suggests that the 334 deletion observed in Gr is responsible for elevated expression in mutant lines and this expression in turn confers the ethylene insensitive phenotypes observed in mutant lines.

Example 5

GR Over-expression Construct and Plant Transformation

Final confirmation that ectopic expression of cLPT12O9 is responsible for conferring the non-ripening phenotype of Grand Nr-2 fruit was achieved through over-expression of the full-length cDNA, derived from Gr/Gr RNA, under the control of the CaMV 35S promoter in transgenic tomato plants. The full-length cDNA sequence of GR derived from Gr/Gr (SEQ ID NO:3) was cloned downstream of the CaMV35S promoter in the binary vector pBI121 modified by removal of the UidA coding region by digestion with BamHI and SacI. The construct was assembled in two pieces due to an internal SacI restriction site. Initially a 5' fragment PCR amplified with the primers GRMUOEF1: 5'-TTTGGATCC AAT-CATTG GTTGAATTTGTTAAAATGGGT-3' (SEQ ID NO:21) and GROER2: 5'-TAAGAGCTCCAACATTAAT-CATGT-3' (SEQ ID NO:22) was cloned into BamHI/SacI digested pBI121 to generate the clone pGRMU5'. A 3' SacI fragment amplified with the primers GROEF2: 5'-ACAT-GATTAATGTTGGAGCTCTTA-3' (SEQ ID NO:23) and GRACFLR1: 5'-TTGAGCTCCAGGAACACTGGACAT-TAACTAAATATA GTAC-3' (SEQ ID NO:24) was inserted into SacI linearized and dephosphorylated pGRMU5'. Construct fidelity was confirmed by DNA sequencing. Transgenic tomato plants were generated through cotyledon-derived explants via Agrobacterium tumefaciens mediated transformation (strain GV3101).

Seventeen out of eighteen primary transformants regenerated from tissue culture displayed a non-ripening phenotype characteristic of the Gr mutant (data not shown). T1 progeny derived from four independently transformed lines, segregating for the NPTII marker gene and GR over-expression, clearly demonstrated a link between the transgene and the non-ripening phenotype (FIG. 2A, B). We have previously documented a weak inhibition of petal senescence associated with the Gr mutant (Barry et al., supra). In support of this observation several of the primary transgenic lines displayed petal retention on developing fruits (FIG. 2C). In addition, ethylene-induced floral abscission is reduced in CaMV35S: GR lines compared to wild type (AC). This response was stronger in flowers of the transgenic lines than in flowers of the Gr mutant (FIG. 2D).

Dark grown hypocotyls of the Gr mutant undergo a normal inhibition of cell elongation in response to ethylene however roots display a slightly reduced response (Barry et al., supra). The triple response phenotype was monitored in two homozygous CaMV35S:GR transgenic lines to determine whether ethylene-insensitivity could be induced in dark grown hypocotyls (FIG. 3A, B). A dose response curve of hypocotyl length in response to increasing concentrations of the ethylene precursor ACC revealed that the CaMV35S:GR lines 4-20 and 6-14 showed a similar pattern of growth inhibition as wild type (AC) and Gr. In contrast, hypocotyls of the partial ethylene-insensitive Nr mutant (Lanahan et al., supra) display reduced inhibition of growth (FIG. 3A). In roots, three phenotypic classes were observed with respect to ethylene-induced growth inhibition (FIG. 3B). Wild type (AC) was most responsive, Gr, 4-20 and 6-14 had an intermediate ethylene response and Nr was least responsive. Given the wild type response of Gr and CaMV35S:GR hypocotyls to ethylene, we monitored GR transcript levels in hypocotyls (FIG. 3C). GR transcripts were undetectable in AC and Nr hypocotyls but were detectable in Gr and were abundant in lines 4-20 and 6-14. These data indicate that ethylene responsiveness is normal in hypocotyls of actively expressing CaMV35S:GR plants. Similar to the response observed in hypocotyls, ethylene-induced petiole epinasty was observed in AC, Gr, 4-20 and 6-14 plants but was greatly reduced in Nr (data not shown). These data again demonstrate that GR is able to regulate ethylene responses in a subset of tomato tissues.

Example 6

A Role for GR During Seed Development

Figure 7:
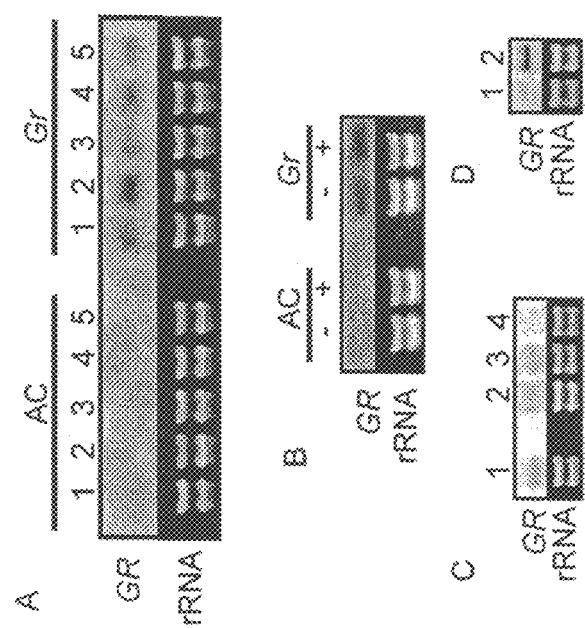
FIGS. 7A-C depict the association of seed development and GR expression.
FIG. 7D shows GR expression in wild type and mutant seeds. Seeds were extracted from immature wild type (1) and Gr (2) fruit. All blots in FIGS. 7A-D contained 15 µg total RNA and were hybridized to a $^{32}$P-labelled GR probe. Images of the rRNA are shown as a guide to equal loading.

Our results indicate that ripening inhibition of Gr is caused by a dominant gain of function mutation that causes elevated expression of GR in mutant fruit (FIGS. 1C, 2A). As a first step to address where GR may be functioning under normal conditions, we examined the expression pattern of GR in various organs and tissues of tomato using RNA gel blot analysis. GR transcripts were undetectable during fruit ripening of wild type fruits but, as suggested by RT-PCR data (FIG. 1B), expression was readily detectable in fruits of the Gr mutant at all stages of development examined (FIG. 7A). Treatment of mature green fruit with ethylene failed to result in a change of GR expression in either wild type or the Gr mutant (FIG. 7B). Furthermore expression was undetectable in leaves of different ages, roots, flowers, and trichomes (data not shown). However, GR transcripts were readily detectable in developing seeds extracted from immature and mature green fruit but not in seeds isolated from ripe fruit (FIG. 7C). Concomitant with increased GR expression in Gr fruit, elevated transcript levels were also observed in immature Gr seed (FIG. 7D). Of note is the slight reduction in transcript size observed in Gr tissues (FIGS. 7C and D). This is in agreement with our data obtained from 5'-RACE experiments, PCR amplification and DNA sequence analysis of the GR locus (FIG. 1D).

Example 7

GR, Member of a Small Gene Family in Higher Plants that is Conserved in Eukaryotes GR encodes a protein of 243 amino acids (SEQ ID NO: 4) with a molecular weight of approximately 27.9 kDa and pI 6.92. A search of several transmembrane domain prediction programs with GR gave variable results with either two or three transmembrane spanning domains predicted depending on the program. A BLASTP search of the predicted GR protein sequence against the Conserved Domain Database ([retrieved on 2005-00-00]. Retrieved from the Internet: <URL: http://www.ncbi.nlm.nih.gov/Structure/cdd/wrpsb.cgi Marchler-Bauer and Bryant (2004. *Nucleic Acid Res.* 32: W327-W331) revealed that GR contains a domain of unknown function (DUF778) that is conserved in several eukaryotic proteins of undetermined biochemical function. A BLASTP search of the GenBank non-redundant CDS database ([retrieved on 2005-00-00]. Retrieved from the Internet: <URL:http://www.ncbi.nlm.nih.gov/BLAST) identified five homologous proteins in plants, two from *Arabidopsis* (At2G26070 and At3G51040) and three from rice (Genbank Accession nos. NP_916598, AAV59409 and AAO37528). Additionally numerous related proteins are present in metazoan genomes having e-values in the range of 1e-17 to 2e-23. No homology was observed to proteins from fungal or bacterial genomes. A TBLASTN search of build three of the solanaceous unigene set (Solanaceous Genomics Network SGN data overview, [online]. Boyce Thomason Institute for Plant Research. Room 221 Tower Road Ithaca N.Y. 14853, USA, [retrieved on 2005-00-00]. Retrieved from the Internet: <URL: www.sgn.cornell.edu) revealed the existence of two additional tomato genes represented by the unigene numbers SGN-U225677 and SGN-U219847 that we have designated GREEN RIPE LIKE 1 and 2 (GRL1 and GRL2) respectively and two potato genes represented by the unigenes SGN-U292599 and SGN-U276841. In addition, the TIGR gene indices ([retrieved on 2005-00-00]. Retrieved from the Internet: <URL: www.tigr.org/tgi) contain several predicted full-length GR-like ESTs from multiple plant species. GR shares 53%, 51% and 37% amino acid identity with GRL1, At2G26070 and GRL2 respectively.

Alignment of GR with several homologous proteins reveals divergence at the N-termini followed by two blocks of approximately 60 amino acids that are highly conserved. An interesting feature of these proteins is that they contain a relatively large number of conserved cysteine and histidine residues throughout the protein (FIG. 5). These are residues that possess high affinity for divalent cations. In addition, GR possesses a single copy of the motif MXCXXC at the carboxy terminus and an MXXXM motif (where X is any hydrophobic residue) in a predicted membrane-spanning domain. These motifs have been shown to participate in the binding of copper ions in the Abel protein of yeast and the copper transport activity of the high affinity copper uptake proteins (Ctr proteins) of human and yeast respectively (Pufahl et al., supra; Puig et al., supra). However, these putative motifs are not conserved in any of the homologous proteins, including GRL1 and GRL2, identified to date.

Phylogenetic analysis indicates that the plant derived proteins form two distinct clades designated group 1 and group 2 (FIG. 6). Distribution of the proteins indicates that higher plants seem likely to possess at least a single protein in each group however rice and tomato each possess a second protein within group 1. In the case of tomato, GR and GRL1 both reside in group 1 and GRL1 has higher homology than GR to At2g26070 (60% versus 51%) suggesting GR is the most novel of the three proteins in tomato as compared to *Arabidopsis*.

Thus, over-expression of GR can modulate ethylene responsiveness in tomato in a predominantly tissue-specific manner that delays fruit ripening and reduces floral senescence and abscission. Therefore, heterologous over-expression of GR can be used to modulate these important agronomic traits in a wide variety of fruit, vegetable and horticultural crops to enhance longevity and prevent spoilage.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated DNA molecule comprising a nucleotide sequence encoding the Green ripe (GR) polypeptide having the amino acid sequence set forth in SEQ ID NO:4.

2. The isolated DNA molecule according to claim 1 wherein said nucleotide sequence is cDNA.

3. The cDNA of claim 2 having the sequence set forth in SEQ ID NO:2.

4. The cDNA of claim 2 having the sequence set forth in SEQ ID NO:3.

5. A recombinant construct comprising the cDNA of claim 4 and one or more regulatory elements operatively linked to said nucleotide sequence wherein expression of said cDNA in a plant results in inhibition of fruit ripening and/or delay in floral senescence and abscission.

6. The recombinant construct of claim 5 wherein said regulatory element is the CaMV 35S promoter.

7. A vector comprising the cDNA of claim 4.

8. An isolated host cell comprising the vector of claim 7.

9. The host cell of claim 8, wherein said host cell is a plant cell.

10. The host cell of claim 9, wherein the plant cell is from a plant selected from the group consisting of *Arabidopsis*, tomato, petunia, rose, carnation, apple, pear, melon, papaya, mango, avocado, banana, stone fruits, and rice.

11. The host cell of claim 9, wherein the plant cell is from a plant selected from the group consisting of *Arabidopsis, Solanum, Lycopersicon, Petunia, Malus, Musa, Prunus*, and *Oryza*.

12. A transgenic plant in which the cDNA according to claim 4 has been introduced or a progeny of said plant in which said cDNA has been introduced and in which expression of SEQ ID NO:4 in said plant or progeny of said plant results in inhibition of fruit ripening or delay of flower senescence or abscission.

13. A transgenic plant comprising plant cells containing a recombinant construct comprising the cDNA of claim 4 and one or more regulatory elements operatively linked to said cDNA wherein expression of said cDNA results in inhibition of fruit ripening and/or delay in floral senescence and abscission.

14. A plant part from the transgenic plant according to claim 13, wherein the plant part contains the recombinant construct.

15. The plant part of claim 14 selected from the group consisting of fruit, petals, abscission zones, and roots.

16. A method of regulating ripening in a plant comprising introducing the nucleotide sequence according to claim 4 into a plant or plant cells and then allowing said nucleotide sequence to be expressed in said plant or plant cells.

17. A method of making a ripening resistant plant, said method comprising: providing a plant cell capable of regeneration; transforming said plant cell with a DNA molecule encoding the Green-ripe (GR) protein of SEQ ID NO:4; culturing said plant cell under plant cell growing conditions; regenerating from aid plant cell a plant; and observing expression of said DNA molecule in said plant, whereby the DNA molecule is expressed at a level sufficient to make a ripening resistant plant.

18. A method of making a ripening-resistant plant, said method comprising: providing a plant cell capable of regeneration; transforming said plant cell with a recombinant construct comprising a regulatory element operable in said plant cell, said regulatory element is operably linked to a DNA molecule encoding the Green-ripe (GR) protein of SEQ ID NO:4; culturing said plant cell under plant cell growing conditions; regenerating from said plant cell a plant; and observing expression of said DNA molecule in said plant, whereby the DNA molecule is expressed at a level sufficient to make a ripening-resistant plant.

19. A ripening-resistant transgenic tomato plant comprising tomato plant cells containing a recombinant construct comprising a regulatory element operable in said plant cells, said regulatory element is operably linked to a DNA molecule encoding the Green-ripe (GR) protein of SEQ ID NO:4, wherein the DNA molecule is expressed at a level sufficient to inhibit ripening.

20. The transgenic plant according to claim 12, wherein the Green-ripe (GR) protein consists of the amino acid sequence set forth in SEQ ID NO:4.

21. A method of manipulating fruit ripening, flower senescence or abscission in a plant or plant cell comprising introducing into a plant or plant cell at least one recombinant construct comprising a cDNA operably linked to a regulatory element that drives expression in a plant or plant cell, wherein said cDNA consists of an isolated nucleic acid molecule comprising a sequence that encodes a polypeptide having the sequence set forth in SEQ ID NO:4.

22. A plant cell, a plant part, or a plant tissue of the plant of claim 12, wherein said plant cell, plant part, or plant tissue comprise the cDNA having the sequence set forth in SEQ ID NO:3 that was introduced into the parent transgenic plant.

23. A transgenic seed of the transgenic plant according to claim 12, wherein said seed comprises the cDNA having the sequence set forth in SEQ. ID NO:3 that was introduced into the parent transgenic plant.

24. A transgenic seed of the transgenic plant according to claim 13, wherein said seed comprises the recombinant construct comprising the cDNA having the sequence set forth in SEQ ID NO:3 that was introduced into the parent transgenic plant.

* * * * *